(12) United States Patent
Fujiwara et al.

(10) Patent No.: US 10,631,759 B2
(45) Date of Patent: Apr. 28, 2020

(54) TESTING INSTRUMENT AND AIRWAY PROTECTION TESTING APPARATUS

(71) Applicants: NATIONAL UNIVERSITY CORPORATION TOTTORI UNIVERSITY, Tottori (JP); CHEST M.I., INCORPORATED, Tokyo (JP)

(72) Inventors: Kazunori Fujiwara, Tottori (JP); Katsuyuki Kawamoto, Tottori (JP); Masaru Ueki, Tottori (JP); Kazutake Uehara, Tottori (JP); Hiroya Kitano, Tottori (JP)

(73) Assignees: National University Corporation Tottori University, Tottori (JP); Chest M.I., Incorporated, Tokyo (JP)

( * ) Notice: Subject to any disclaimer, the term of this patent is extended or adjusted under 35 U.S.C. 154(b) by 420 days.

(21) Appl. No.: 15/522,740

(22) PCT Filed: Oct. 28, 2015

(86) PCT No.: PCT/JP2015/080350
§ 371 (c)(1),
(2) Date: Apr. 27, 2017

(87) PCT Pub. No.: WO2016/068172
PCT Pub. Date: May 6, 2016

(65) Prior Publication Data
US 2017/0273598 A1    Sep. 28, 2017

(30) Foreign Application Priority Data
Oct. 31, 2014    (JP) .................................. 2014-223697

(51) Int. Cl.
*A61B 5/097* (2006.01)
*A61B 5/08* (2006.01)
*A61B 5/087* (2006.01)

(52) U.S. Cl.
CPC ................ *A61B 5/097* (2013.01); *A61B 5/08* (2013.01); *A61B 5/087* (2013.01); *A61B 5/0823* (2013.01)

(58) Field of Classification Search
CPC ........... A61B 5/097; A61B 5/08; A61B 5/087; A61B 5/0823
See application file for complete search history.

(56) References Cited

U.S. PATENT DOCUMENTS 9,180,271 B2 * 11/2015 Guo .................. A61M 16/0816
2005/0245837 A1 * 11/2005 Pougatchev ........... A61B 5/097
600/538

(Continued)

FOREIGN PATENT DOCUMENTS

DE     202011005437 U1    6/2011
JP     S63-242228 A       10/1988

(Continued)

OTHER PUBLICATIONS

Search Report issued in corresponding International Patent Application No. PCT/JP2015/080350, dated Jan. 26, 2016.

(Continued)

*Primary Examiner* — Devin B Henson
(74) *Attorney, Agent, or Firm* — McDermott Will & Emery LLP

(57) ABSTRACT

According to an aspect, a testing instrument that is used for testing an airway protection function includes: a pipe portion continuous from an inlet port to an outlet port, the pipe portion having a plurality of holes penetrating the pipe portion from an outer surface of the pipe portion to an inner surface of the pipe portion, the holes being provided for guiding a reagent gas mixture to the inside of the pipe portion; and a guide portion covering all of the holes to form (Continued)

a closed space and guiding the reagent gas mixture to the closed space from an inflow port.

16 Claims, 15 Drawing Sheets

(56) References Cited

U.S. PATENT DOCUMENTS

| | | | |
|---|---|---|---|
| 2007/0123793 A1 | 5/2007 | Addington et al. | |
| 2013/0267864 A1* | 10/2013 | Addington | A61B 5/4839 |
| | | | 600/538 |

FOREIGN PATENT DOCUMENTS

| | | |
|---|---|---|
| JP | H06-121785 A | 5/1994 |
| JP | 2008-301895 A | 12/2008 |
| JP | 3158906 U | 4/2010 |
| JP | 2013-017694 A | 1/2013 |

OTHER PUBLICATIONS

International Preliminary Report on Patentability issued in corresponding International Patent Application No. PCT/JP2015/080350, dated May 4, 2017.
Extended Search Report issued issued in EP Patent Application No. 15854008.8, dated Jun. 7, 2018.
J. K. Gupta et al., "Flow Dynamics and Characterization of a Cough:", Indoor Air, 19(6): pp. 517-525 (2009).

\* cited by examiner

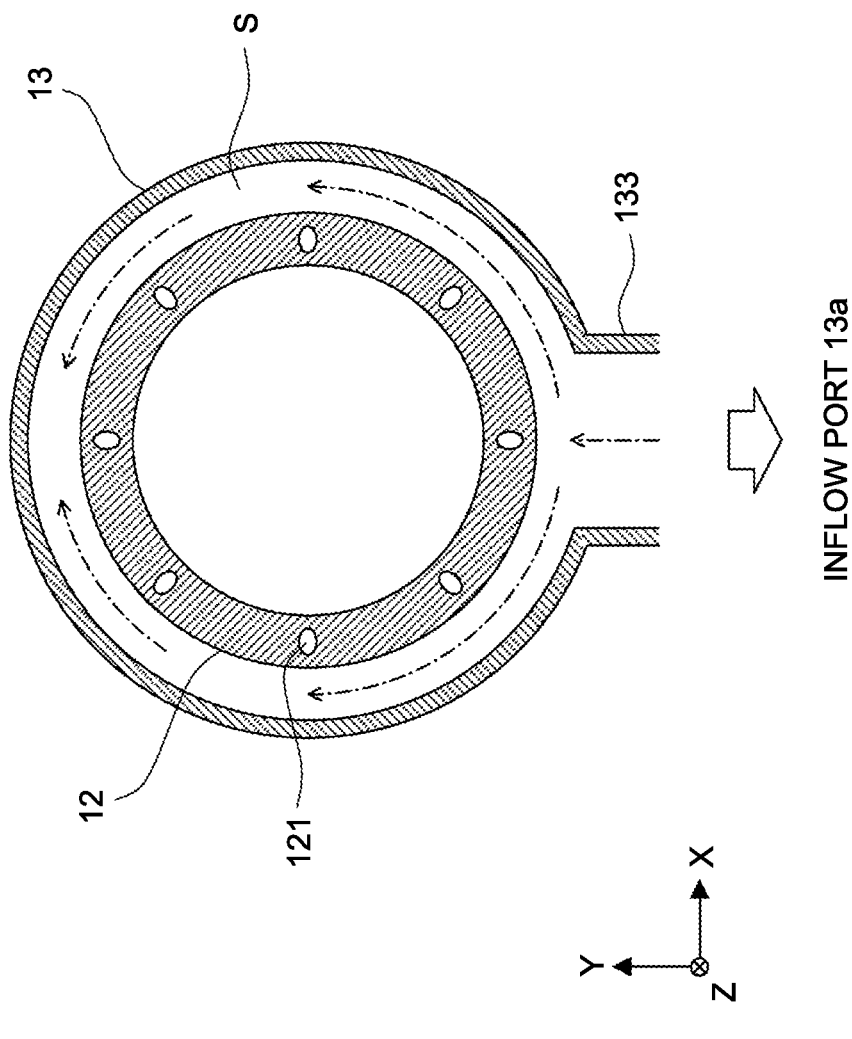

FIG.4A

NORMAL EXAMPLE

| AGE | SEX | FVC(L) | PCF(L/s) | time(s) |
|---|---|---|---|---|
| 29 | MALE | 1.08 | 5.75 | 1 |
| 31 | MALE | 1.15 | 4.05 | 1 |
| 38 | MALE | 1.31 | 5.21 | 1 |
| 27 | MALE | 1.45 | 4.8 | 1 |
| 32 | FEMALE | 0.43 | 3.16 | 1 |
| 28 | FEMALE | 0.6 | 2.5 | 1 |

FIG.4B

EXAMPLE WITH PAST HISTORY OF PNEUMONIA

| AGE | SEX | FVC(L) | PCF(L/s) | time(s) |
|---|---|---|---|---|
| 75 | MALE | 0.17 | 0.2 | 25 |
| 69 | FEMALE | 0.85 | 0.49 | 25 |
| 74 | MALE | 1.48 | 0.32 | 22 |

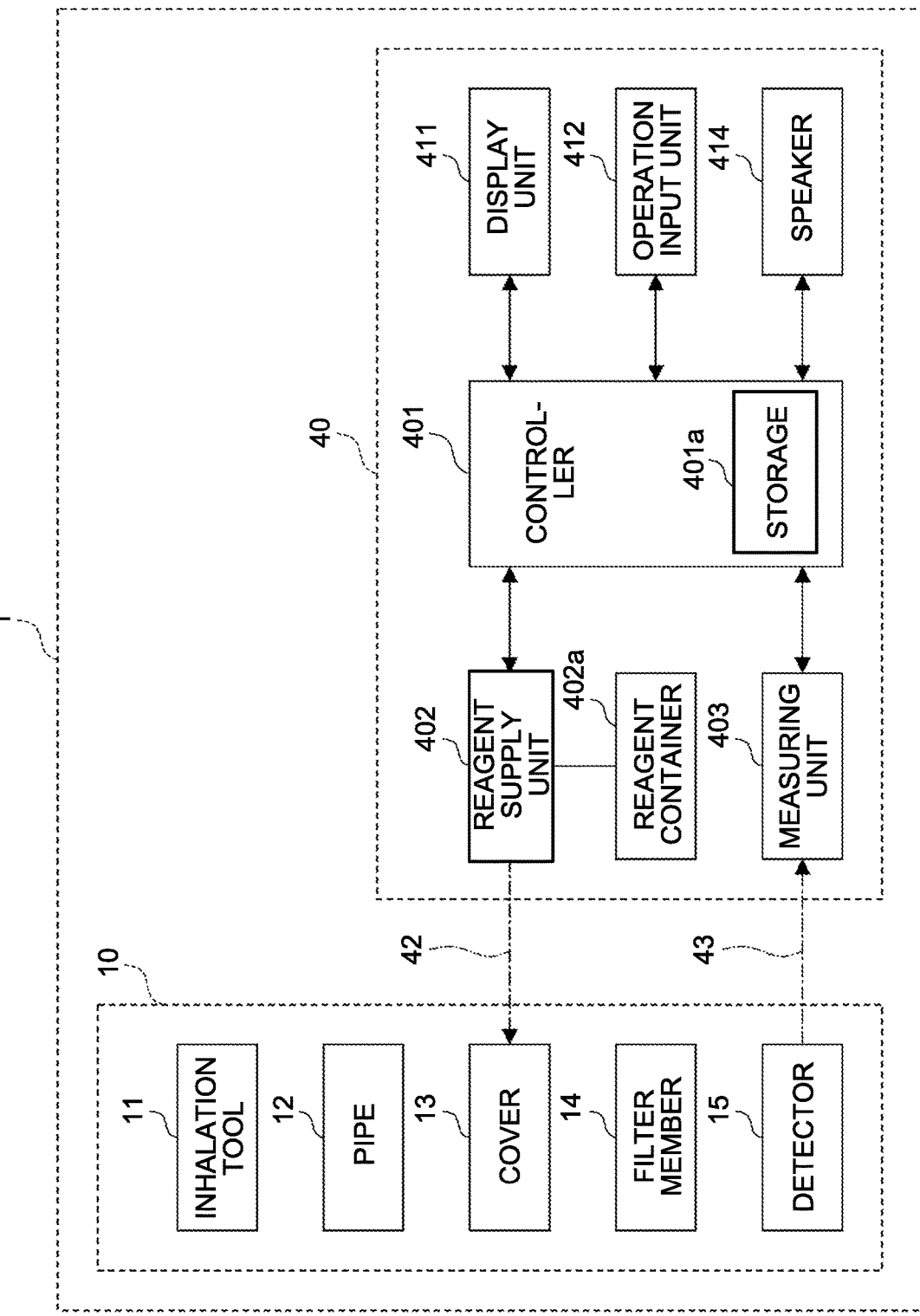

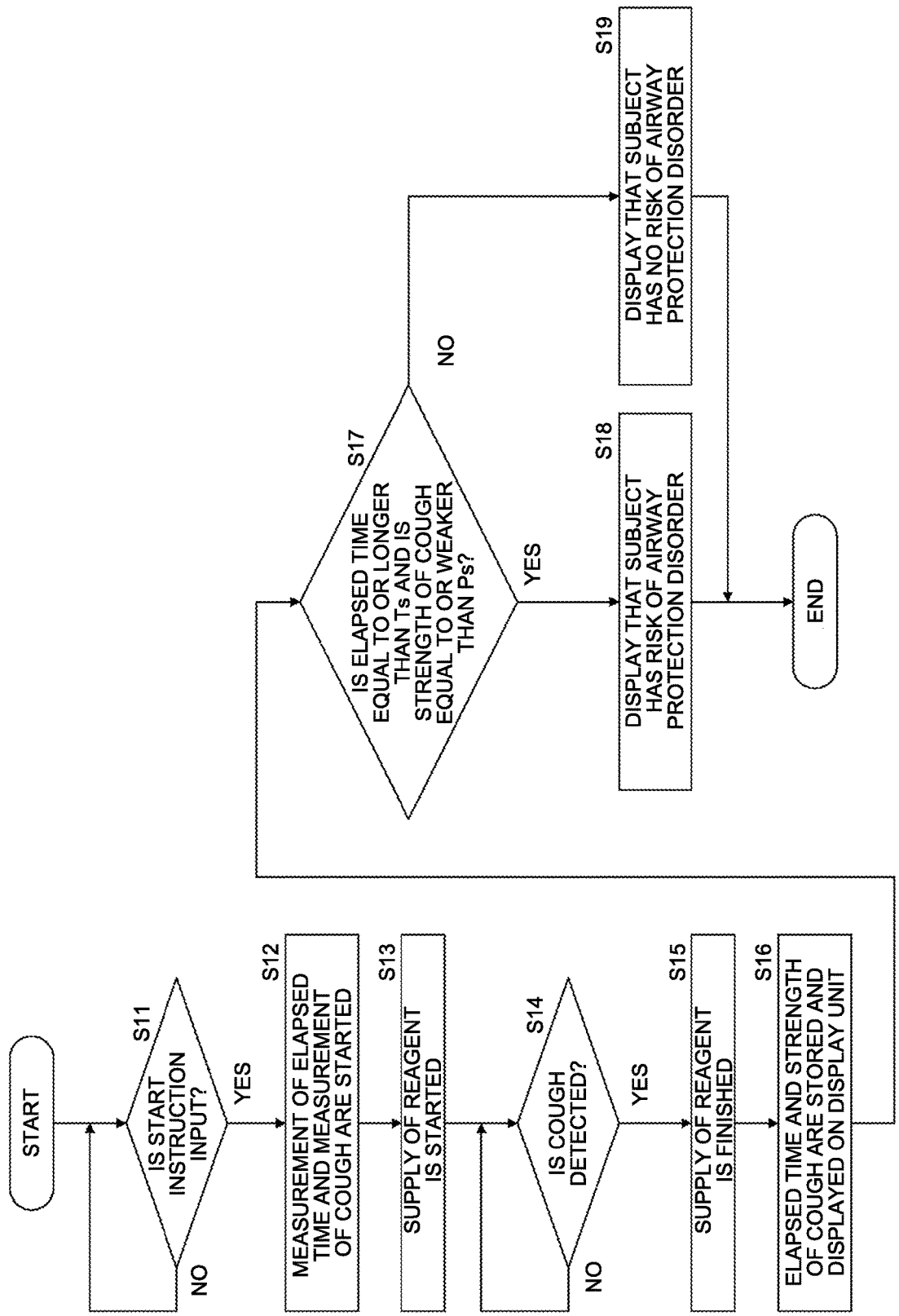

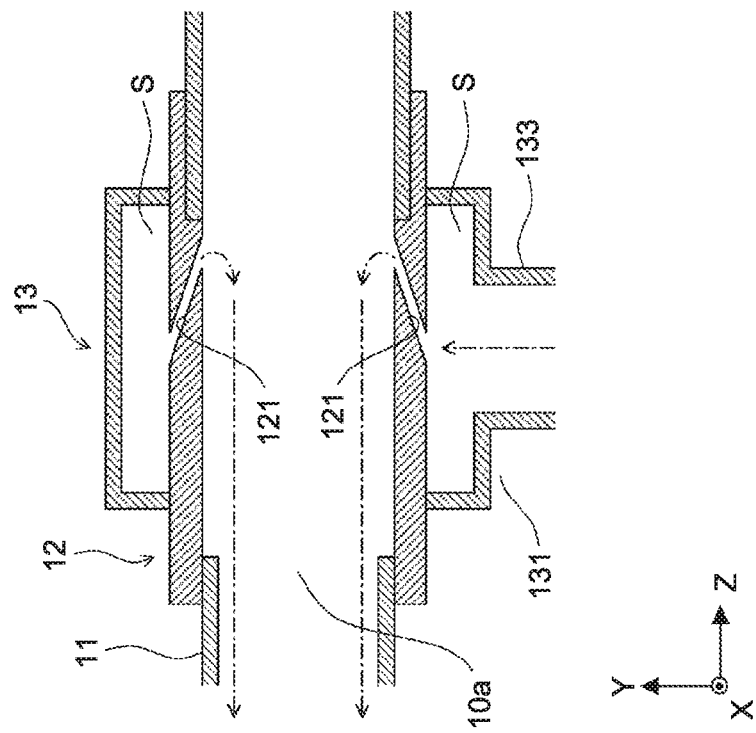
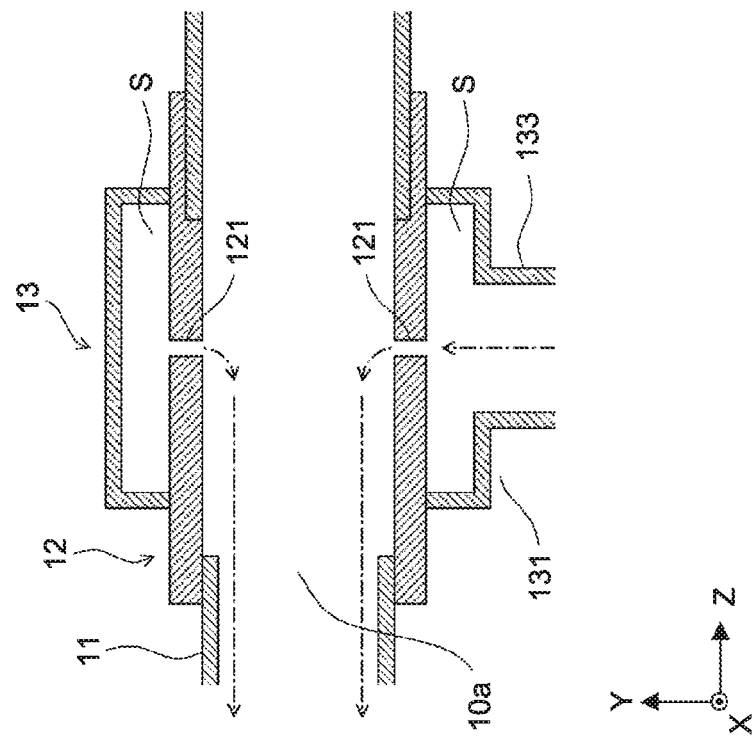

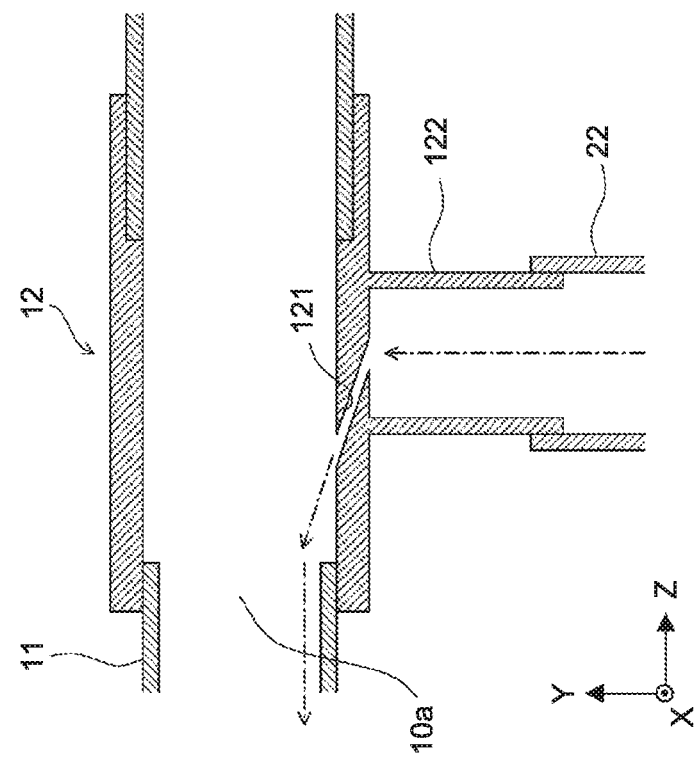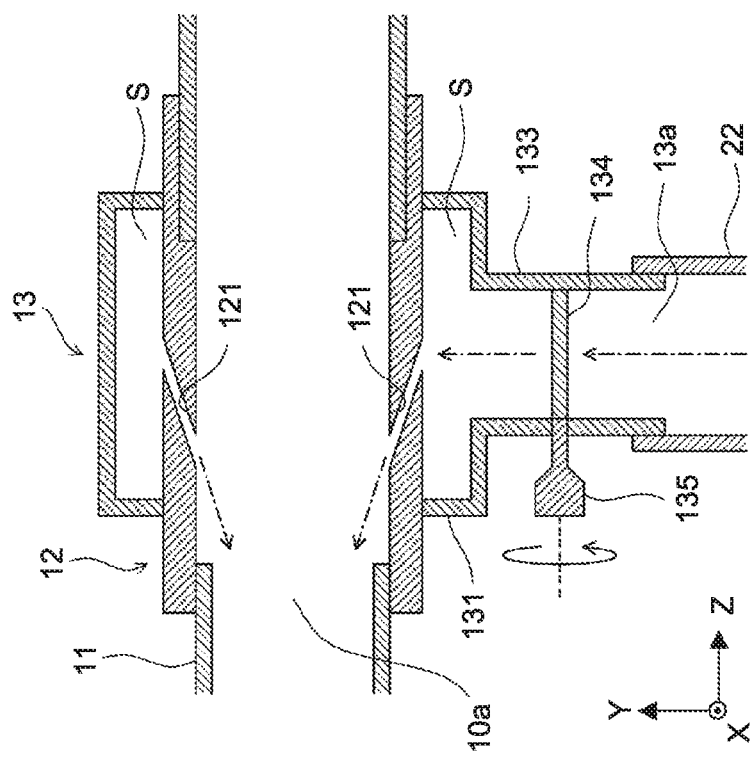

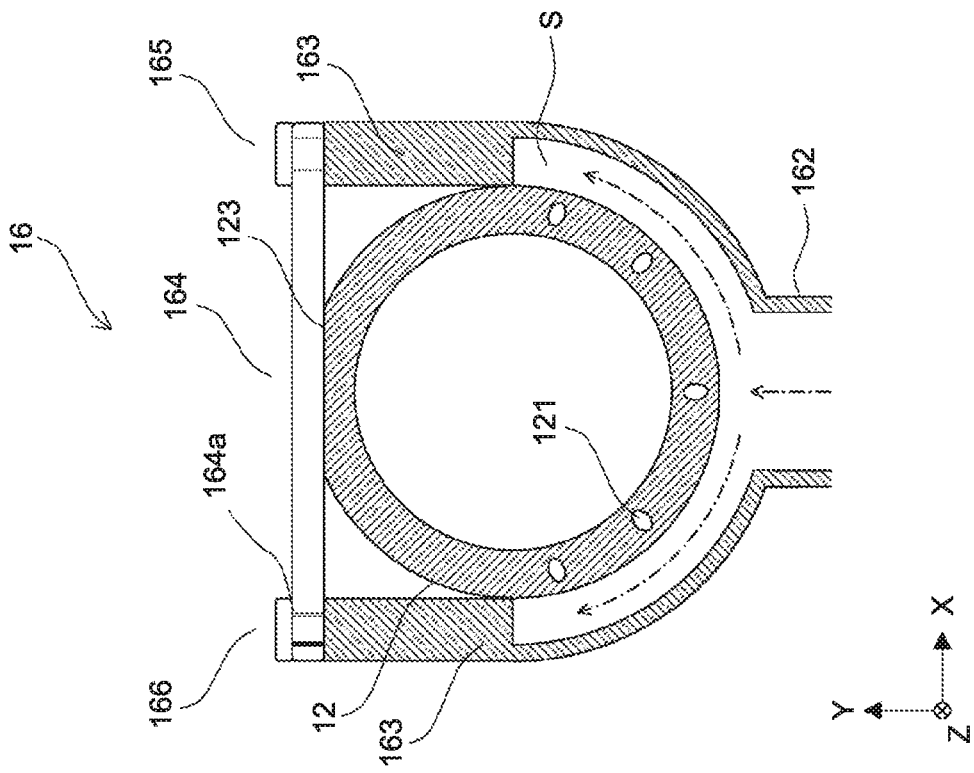
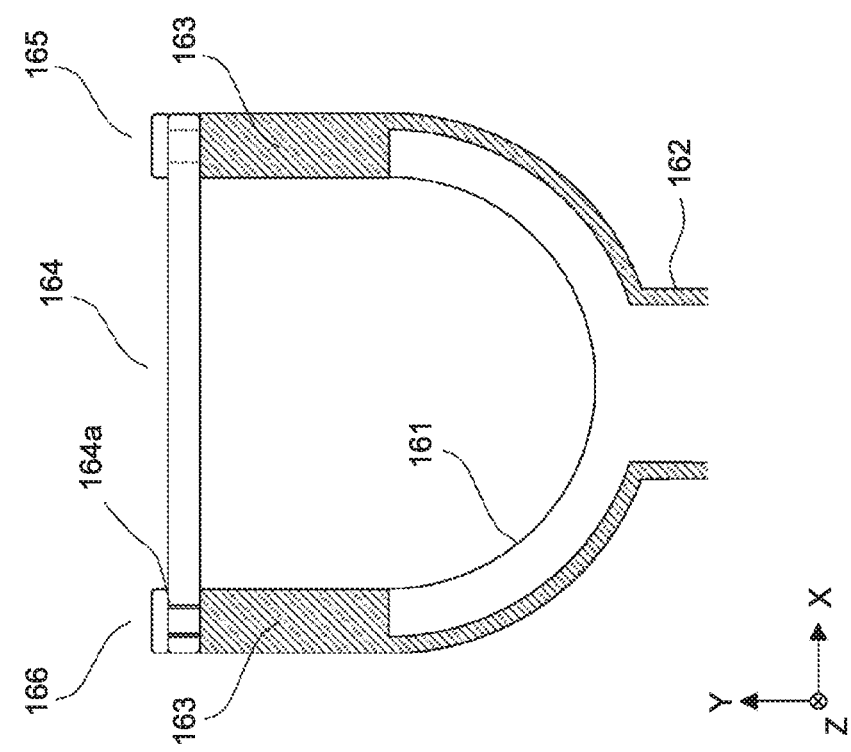

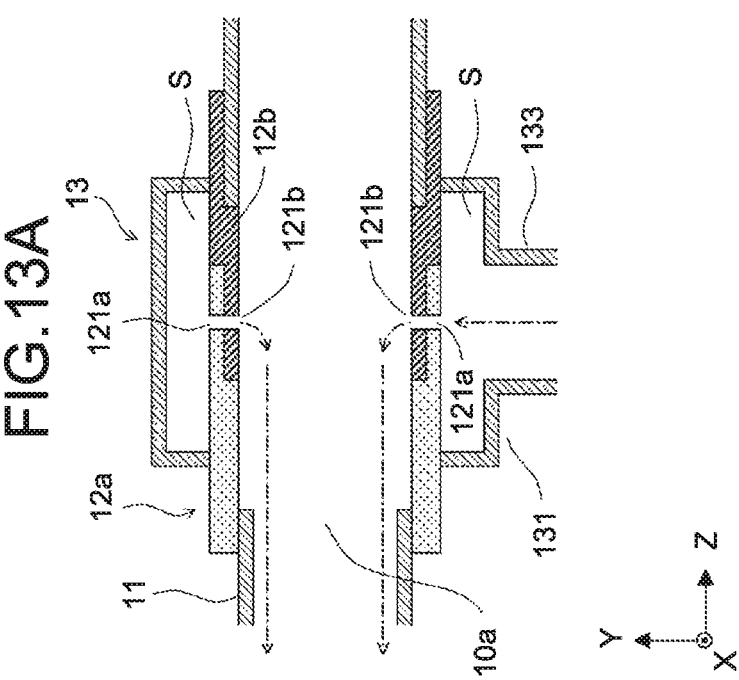
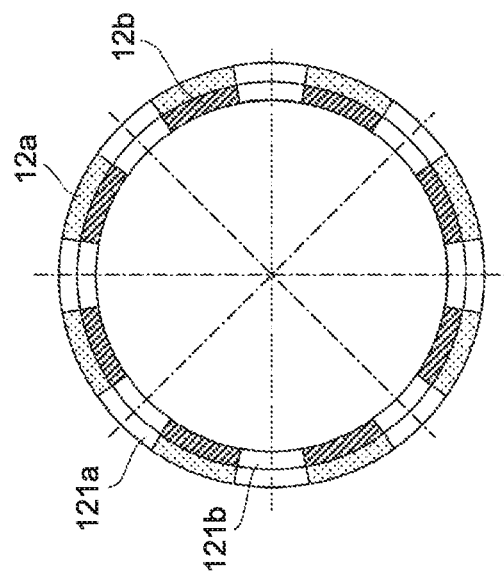
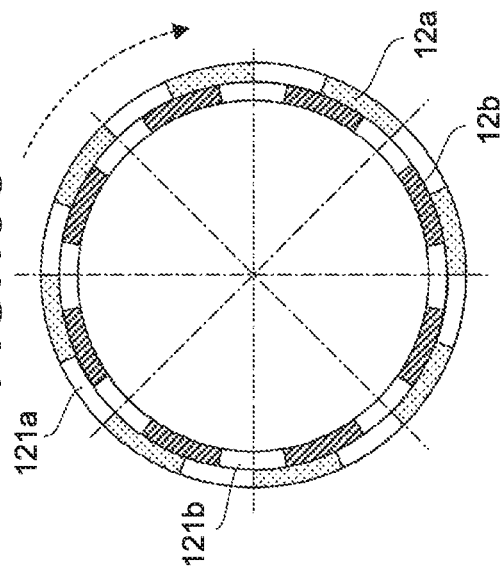

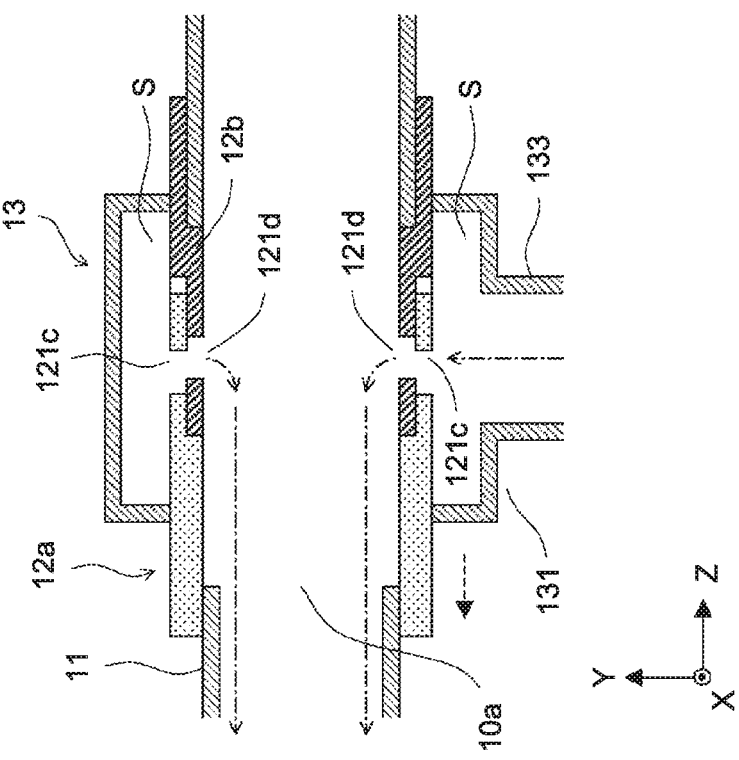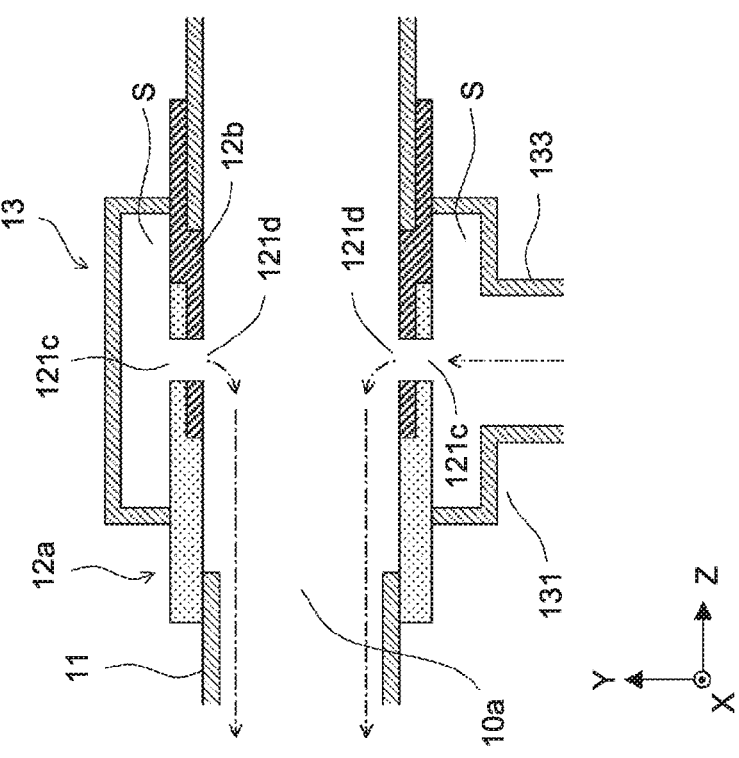

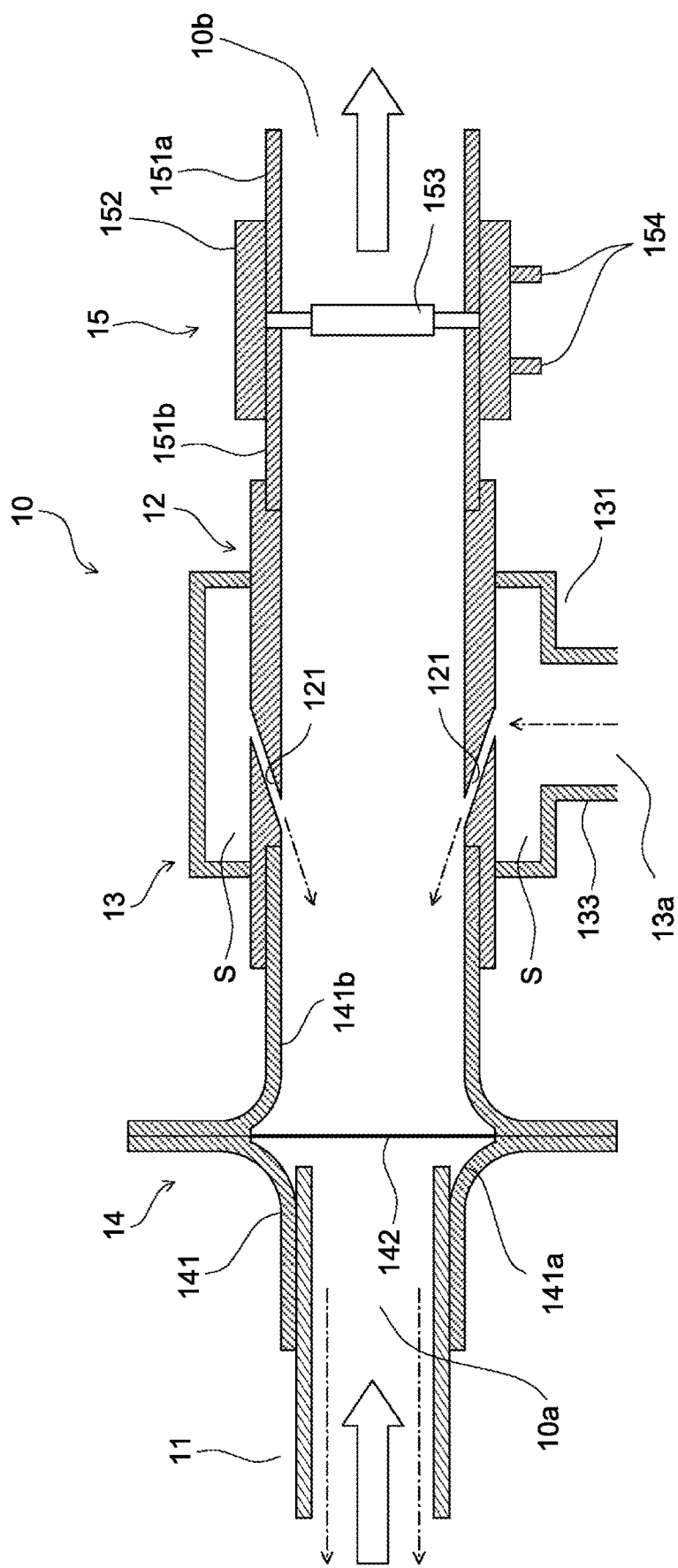

TESTING INSTRUMENT AND AIRWAY PROTECTION TESTING APPARATUS

CROSS REFERENCE TO RELATED APPLICATION

This application is a National Stage of PCT International Application Ser. No. PCT/JP2015/080350 filed on Oct. 28, 2015 which designates the United States, and which is based upon and claims the benefit of priority from Japanese Patent Application No. 2014-223697 filed on Oct. 31, 2014, the entire contents of which are incorporated herein by reference.

FIELD

The present invention relates to a testing instrument and an airway protection testing apparatus that are used for testing an airway protection function.

BACKGROUND

Currently, of the total number of patients in medical institutions, 1.6% patients are estimated to be under treatment for aspiration pneumonia. It is considered that mortality of patients who repeatedly contract aspiration pneumonia is high. In particular, mortality of elderly people due to aspiration pneumonia is extremely high. Conventionally, various methods for testing a swallowing state have been studied (for example, Patent Literatures 1 and 2).

CITATION LIST

Patent Literature

Patent Literature 1: Japanese Patent Application Laid-open No. 2013-017694
Patent Literature 2: Japanese Patent Application Laid-open No. 2008-301895

SUMMARY

Technical Problem

In general, aspiration is caused by a lowering of the sensitivity of the pharynx and a lowering of the ability to expel foreign bodies that are about to enter the airway. Accordingly, it is important in the prevention of aspiration pneumonia to test these elements. With the methods disclosed in Patent Literatures 1 and 2 mentioned above, whether a swallowing operation functions properly is determined based on a change in the position of the pharynx and swallowing sound. These methods, however, cannot test the basic elements of aspiration that are the sensitivity of the pharynx and the ability to expel foreign bodies, i.e., the airway protection function cannot be tested.

In consideration of the above-mentioned problems, an object of the present invention is to provide a testing instrument and an airway protection testing apparatus capable of easily and smoothly testing the airway protection function.

Solution to Problem

A first aspect of the present invention relates to a testing instrument that is used for testing an airway protection function. The testing instrument according to the aspect includes: a pipe portion continuous from an inlet port to an outlet port; at least one hole penetrating the pipe portion from an outer surface of the pipe portion to an inner surface of the pipe portion; and a guide portion covering the hole and guiding a reagent gas mixture to the hole from an inflow port.

With the testing instrument according to the aspect, when the reagent gas mixture is supplied from the inflow port, the gas mixture is guided to the hole and is further guided to the inlet port while passing through the inside of the pipe portion from the hole. Accordingly, a subject can inhale the reagent through the inlet port. When the reagent is inhaled, then, due to the reagent, the subject is induced to cough. When the subject coughs, airflow of the cough travels from the inlet port toward the outlet port while passing through the inside of the pipe portion. Strength of the thus induced cough can therefore be measured by disposing a sensor detecting the airflow of the cough that flows toward the outlet port. Time until the subject coughs can be measured manually or measured automatically based on output from the sensor.

Usage of the testing instrument according to the first aspect enables elapsed time until induction of the cough and the strength of the cough to be measured simultaneously. The elapsed time corresponds to sharpness of the sensitivity of the pharynx, and the shorter elapsed time indicates the sharper sensitivity of the pharynx. The strength of the cough mainly corresponds to the ability to expel foreign bodies, and the stronger cough indicates the higher ability to expel foreign bodies. Thus, usage of the testing instrument according to the first aspect makes it easy and smooth to obtain information related to basic elements necessary for determining an airway protection function.

The cough caused by using the testing instrument according to the first aspect is not a voluntary cough intended by the subject but an involuntary cough reflexively caused by the reagent. Measurement of the involuntary cough enables the sensitivity of the pharynx and the ability to expel foreign bodies to be grasped as the original airway protection function of the subject. Accordingly, the airway protection function of the subject can be properly diagnosed by using the testing instrument according to the first aspect.

In the testing instrument according to the aspect, an inhalation tool to be held in the mouth of a subject may be installed on the inlet port in a detachable manner, for example. With this configuration, the inhalation tool can be appropriately replaced, thereby testing the airway protection function hygienically.

The testing instrument according to the aspect may include a sensor for detecting strength of airflow that is discharged from the outlet port. With this configuration, time and effort for separately mounting a sensor on the testing instrument are eliminated.

In the testing instrument according to the aspect, the guide portion can be detachable from the pipe portion. In this case, when the guide portion is mounted on the pipe portion, a closed space can be formed around the hole, and the closed space and the inflow port can communicate with each other.

For example, the guide portion may have an opening into which the pipe portion is fit in a detachable manner, and has such a shape that, when the pipe portion is fit into the opening, the closed space is formed around the hole, and a closed space and the inflow port communicate with each other. When the guide portion is detachable from the pipe portion, the guide portion is appropriately detached from the pipe portion, and then the guide portion and the pipe portion can be cleaned by washing or the like. Accordingly, the testing instrument can be kept hygienic, and clogging of the hole can be prevented by cleaning.

In the testing instrument according to the aspect, it is preferable that the pipe portion has a plurality of the holes. With this configuration, the proper amount of reagent can be smoothly introduced into the pipe portion when the reagent is inhaled while reducing the size of the individual holes. Furthermore, the reduction in size of the individual holes can prevent the airflow generated by the subject's cough from leaking into the guide portion through the holes. The airflow of the cough can therefore be smoothly guided to the outlet port of the pipe portion, thereby measuring the strength of the cough with high accuracy.

The hole may be formed so as to gradually become closer to the inlet port as the hole approaches the inner surface of the pipe portion from the outer surface of the pipe portion. Thus, the reagent gas mixture can be made to smoothly travel toward the inlet port when the reagent is inhaled.

Alternatively, the hole may be formed so as to gradually become farther from the inlet port as the hole approaches the inner surface of the pipe portion from the outer surface of the pipe portion. Thus, airflow generated by the subject's cough is difficult to leak into the guide portion from the hole. The airflow of the cough can therefore be smoothly guided to the outlet port of the pipe portion, thereby measuring the strength of the cough with high accuracy.

The testing instrument according to the aspect may further include: a stopper blocking a flow path continuous from the inflow port to the hole; and an opening and closing member opening and closing the stopper. With this configuration, timing at which the reagent is caused to travel to the inlet port can be controlled using the opening and closing member. The elapsed time until induction of the cough can therefore be measured more properly.

A second aspect of the present invention relates to an airway protection testing apparatus. The airway protection testing apparatus according to the aspect, includes: the testing instrument according to the first aspect; a reagent supply unit supplying the reagent gas mixture to the inflow port; a measuring unit measuring strength of airflow that is discharged from the outlet port; and a display unit displaying information based on a measurement result obtained by the measuring unit.

With the airway protection testing apparatus according to this aspect, a test is performed using the testing instrument according to the first aspect. Accordingly, the elapsed time until induction of the cough and the strength of the cough can be simultaneously measured as in the first aspect. This enables information related to the basic elements necessary for determining the airway protection function to be obtained easily and smoothly. Furthermore, the information based on the strength of the airflow is displayed on the display unit. This display enables a physician, an examiner, or the like to determine whether the subject has a disorder in the airway protection function by checking the display.

In the airway protection testing apparatus according to the aspect, the measuring unit may further measure elapsed time until the airflow is generated in the outlet port after the gas mixture starts to be supplied to the inflow port, and the display unit may further display information based on the time. With this configuration, a physician, an examiner, or the like can simultaneously grasp the strength of the airflow generated by the cough and the elapsed time until induction of the cough by checking the display on the display unit. In addition, time and effort for measuring the elapsed time manually can be saved. Accordingly, whether the subject has the disorder in the airway protection function can be smoothly and easily determined.

When the elapsed time until induction of the cough is further measured, the measuring unit may determine a risk of an airway protection disorder based on the strength of the airflow and the elapsed time, and the display unit may display information based on a determination result of the risk. With this configuration, the risk of the airway protection disorder can be easily grasped also in nursing and caring facility and the like in which there is no person who has expert knowledge, such as a physician and an examiner. Persons in charge in the nursing and caring facility and the like can therefore take measures of causing the subject having the risk of the airway protection disorder to undergo medical examination by a specialist and so on appropriately, thereby reducing the possibility that the subject suffers from aspiration pneumonia.

The airway protection testing apparatus according to the aspect, the testing instrument, the reagent supply unit, the measuring unit, and the display unit may be accommodated in one housing. With this configuration, the airway protection testing apparatus can be easily carried and a test operation can be easily performed.

Advantageous Effects of Invention

As described above, the present invention can provide a testing instrument and an airway protection testing apparatus capable of easily and smoothly testing an airway protection function.

Characteristics of the present invention will be made clearer by the following description of embodiments. The following embodiments are merely modes for carrying out the present invention, and the present invention or the meanings of terminologies of its components are not limited by those described in the following embodiments.

BRIEF DESCRIPTION OF DRAWINGS

FIG. 3 is a cross-sectional view illustrating the configuration of the testing instrument according to the first embodiment.

FIG. 4A and FIG. 4B include tables illustrating test results obtained by the airway protection testing apparatus according to the first embodiment.

FIG. 6 is a diagram illustrating the configuration of the airway protection testing apparatus according to the second embodiment.

FIG. 7 is a flowchart illustrating control of the airway protection testing apparatus according to the second embodiment.

FIG. 10A and FIG. 10B include sectional views each illustrating the configuration of a testing instrument according to a modification.

FIG. 11A and FIG. 11B include sectional views each illustrating the configuration of a testing instrument according to another modification.

FIG. 12A and FIG. 12B include cross-sectional views each illustrating the configuration of a testing instrument according to still another modification.

FIG. 13A, FIG. 13B, and FIG. 13C include cross-sectional views and a sectional view each illustrating the configuration of a testing instrument according to still another modification.

FIG. 14A and FIG. 14B include sectional views each illustrating the configuration of a testing instrument according to still another modification.

FIG. 15 is a sectional view illustrating the configuration of a testing instrument according to still another modification.

Figure 1:
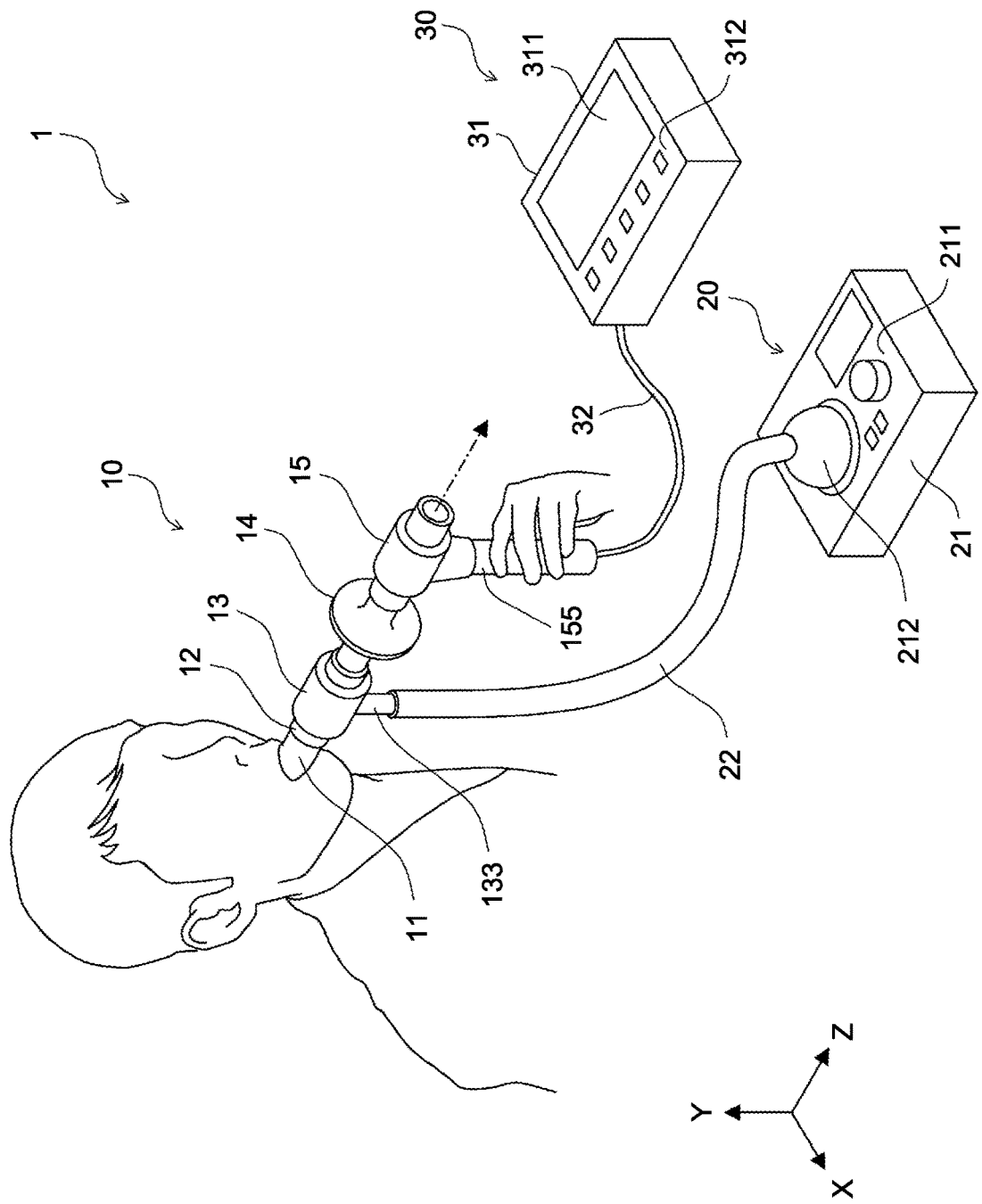
FIG. 1 is a view illustrating the configuration of an airway protection testing apparatus according to a first embodiment.

It should be noted that the drawings are provided merely for explanation and do not limit the scope of the present invention.

DESCRIPTION OF EMBODIMENTS

Hereinafter, embodiments of the present invention will be described with reference to the drawings. An X axis, a Y axis, and a Z axis, which are orthogonal to one another, are added to the drawings for the convenience of description. The X axis and the Y axis are parallel to a horizontal plane and the Z axis is parallel to the vertical direction.

First Embodiment

In a first embodiment, a "pipe portion" described in the claims is constructed from a pipe 12, a support portion 141 of a filter member 14, and cylindrical members 151a and 151b of a detector 15. A cover 13 in the first embodiment corresponds to a "guide portion" described in the claims, and a reagent supply unit 20 and a measuring unit 30 correspond to a "reagent supply unit" and a "measuring unit" described in the claims, respectively. The first embodiment exemplifies a mode for carrying out the invention described in the claims and the invention described in the claims is not limited by correspondence between the configuration in the above-mentioned first embodiment and the configuration in the claims.

FIG. 1 is a perspective view illustrating the configuration of an airway protection testing apparatus 1 according to the first embodiment.

As illustrated in FIG. 1, the airway protection testing apparatus 1 includes a testing instrument 10, the reagent supply unit 20, and the measuring unit 30. A reagent gas mixture is supplied to the testing instrument 10 from the reagent supply unit 20. The reagent is tartaric acid, and the gas mixture, obtained by mixing droplets of tartaric acid with the air, is generated in the reagent supply unit 20. The testing instrument 10 includes an inhalation tool 11, the pipe 12, the cover 13, the filter member 14, and the detector 15.

Figure 2A:
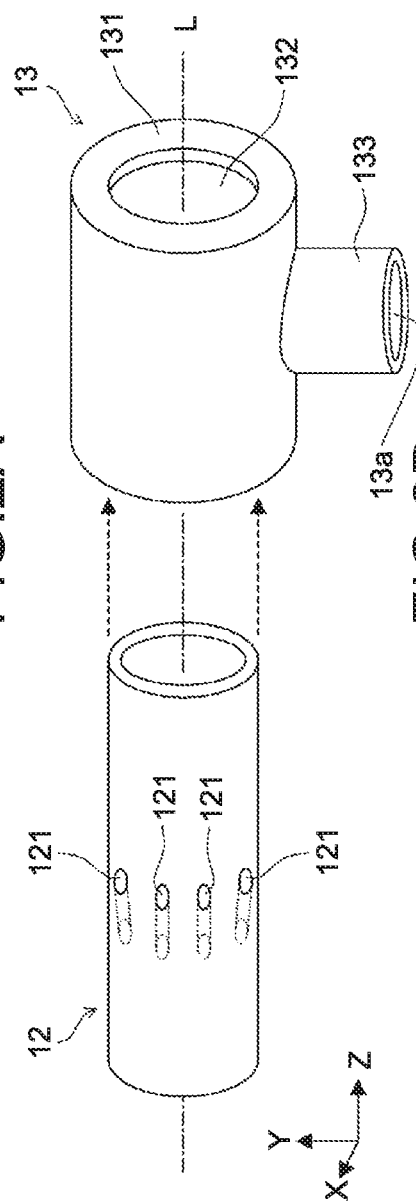
FIG. 2A includes a view illustrating the configurations of a pipe and a cover according to the first embodiment, and FIG. 2B includes a sectional view illustrating the configuration of a testing instrument.

FIG. 2(a) is a view illustrating the configurations of the pipe 12 and the cover 13.

The pipe 12 is made of a resin material and has a cylindrical shape. The pipe 12 has a plurality of holes 121 penetrating the pipe 12 from the outer surface to the inner surface. These holes 121 are formed so as to be aligned at a constant interval in the circumferential direction of the pipe 12. The plurality of holes 121 are arranged in the pipe 12 evenly in the circumferential direction.

The cover 13 is formed with a cylindrical member having an outer diameter that is larger than that of the pipe 12. The cover 13 is also made of the resin material. The length of the cover 13 in the Z-axis direction is smaller than the length of the pipe 12 in the Z-axis direction. Flange portions 131 are provided on the respective end edges of the cover 13 at the sides facing in the negative and positive directions of the Z-axis so as to extend toward a center axis L of the cover 13. A circular opening 132 is formed at the inner side of each of the flange portions 131. The center of each opening 132 is identical to the center axis L of the cover 13. The diameter of each opening 132 is substantially the same as the outer diameter of the pipe 12.

The pipe 12 and the cover 13 are integrated with each other by fitting the pipe 12 into the openings 132. The integrated cover 13 can be appropriately detached from the pipe 12. A cylinder portion 133 is formed on the lower surface of the cover 13. A space in the cylinder portion 133 communicates with a space in the openings 132. The lower end of the cylinder portion 133 corresponds to an inflow port 13a for the reagent gas mixture.

Figure 2B:
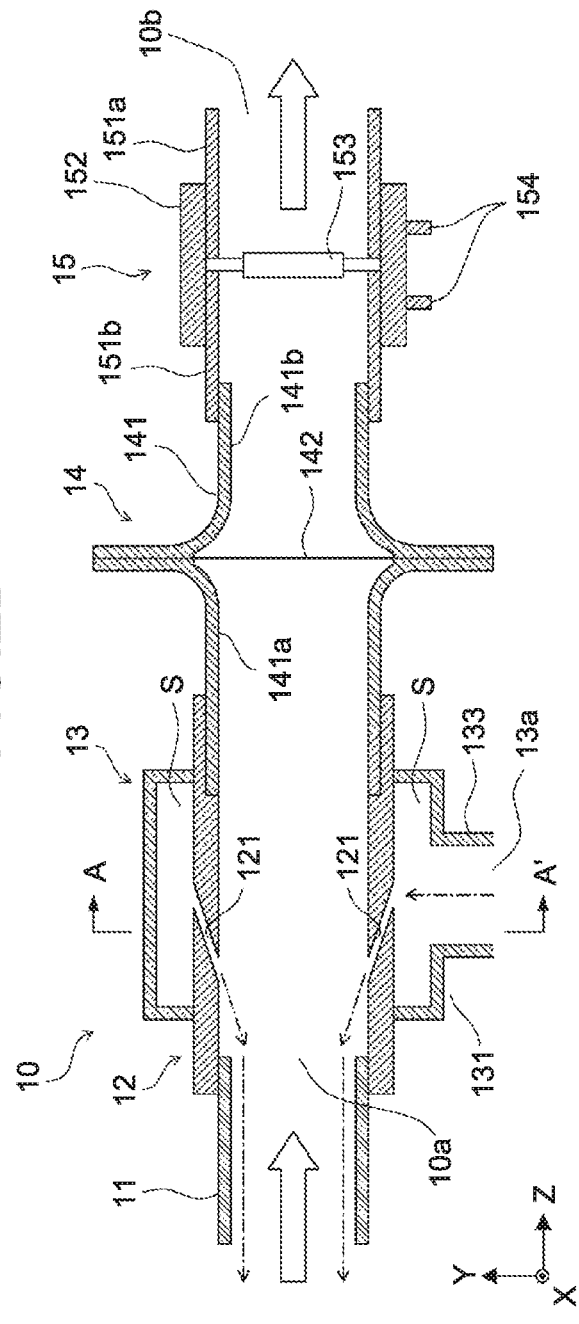

FIG. 2(b) is a sectional view when the testing instrument 10 illustrated in FIG. 1 is evenly cut along a plane that is parallel to the Y-Z plane. FIG. 3 is a cross-sectional view cut along line A-A' in FIG. 2(b).

As illustrated in FIG. 2(b), the cover 13 is mounted on the pipe 12 so as to cover the holes 121 from the outer side of the pipe 12. With this mounting, as illustrated in FIG. 2(b) and FIG. 3, a closed space S is formed around the holes 121, and the inflow port 13a communicates with the closed space S. When the reagent gas mixture is introduced to the inflow port 13a, the closed space S is filled with the gas mixture, and the gas mixture is further guided into the pipe 12 from the closed space S through the holes 121.

The end edge of the pipe 12 at the side facing in the negative direction of the Z-axis corresponds to an inlet port 10a for enabling a subject to inhale the gas mixture. As illustrated in FIG. 2(b), the cylindrical inhalation tool 11 is fit into the inlet port 10a. The inhalation tool 11 is made of, for example, a paper material having a predetermined thickness so as to be disposable. Alternatively, the inhalation tool 11 may be made of another material such as a resin material.

As illustrated in FIG. 2(b), in the first embodiment, the holes 121 are formed so as to gradually become closer to the inlet port 10a as the holes 121 approach the inner surface of the pipe 12 from the outer surface thereof. The gas mixture accumulated in the closed space S smoothly travels toward the inlet port 10a.

As illustrated in FIG. 2(b), the filter member 14 is mounted on the end edge of the pipe 12 at the side facing in the positive direction of the Z-axis. The filter member 14 includes the support portion 141 and a filter 142. The support portion 141 is made of a resin material and has such a shape that a center portion of a cylinder projects radially over the entire circumference. The support portion 141 is configured by combining two cylindrical members 141a and 141b having the sectional shapes illustrated in FIG. 2(b). The two cylindrical members 141a and 141b of the support portion 141 pinch the outer circumferential portion of the filter 142 such that the filter 142 is supported by the support portion 141. The two cylindrical members 141a and 141b are bonded to each other with an adhesive in a state of pinching the filter 142 in this manner. A space in the support portion 141 is divided by the filter 142 at a center portion in the Z-axis direction. The filter 142 filters the air flowing in the positive direction of the Z-axis in the support portion 141.

The inner diameter of the support portion 141 at the side facing in the negative direction of the Z-axis is substantially the same as the inner diameter of the pipe 12. A step is provided on the end edge of the pipe 12 at the side facing in the positive direction of the Z-axis, and the end edge of the support portion 141 at the side facing in the negative direction of the Z-axis is fit into the step such that the filter member 14 is integrated with the pipe 12. The integrated filter member 14 can be appropriately pulled out and detached from the pipe 12.

In addition, as illustrated in FIG. 2(b), the detector 15 is mounted on the end edge of the support portion 141 at the side facing in the positive direction of the Z-axis. The detector 15 includes the two cylindrical members 151a and 151b having cylindrical shapes that are fit into a holding member 152 having a cylindrical shape. The cylindrical members 151a and 151b and the holding member 152 are made of a resin material. Furthermore, a predetermined support member supports a sensor 153 detecting strength of airflow in the holding member 152. There is a space between the circumference of the sensor 153 and the cylindrical members 151a and 151b when seen along the Z-axis direction, and the airflow can pass through the space. The sensor 153 is connected to terminals 154 with wirings (not illustrated). For example, a piezoelectric element is used as the sensor 153.

The detector 15 is integrated with the filter member 14 by fitting the cylindrical member 151b at the side facing in the negative direction of the Z-axis with an end portion of the support portion 141 at the side facing in positive direction the Z-axis. The testing instrument 10 illustrated in FIG. 1 is configured in this manner. As illustrated in FIG. 1, a grip 155 is mounted on the lower surface of the holding member 152 so as to cover the terminals 154.

By referring to FIG. 1 again, the reagent supply unit 20 generates the gas mixture obtained by mixing the fine droplets of tartaric acid with the air. The reagent supply unit 20, for example, has the same function and configuration as those of an existing nebulizer. The reagent supply unit 20, for example, generates fine droplets by the principle of spray with high-speed airflow or makes the reagent into droplets with an ultrasonic oscillator, and then generates the gas mixture by causing the droplets to flow on the air from a fan.

The reagent supply unit 20 has a configuration in which an operation input unit 211 and a spray unit 212 are provided on the upper surface of a box-shaped main body 21. The spray unit 212 discharges the gas mixture generated in the reagent supply unit 20. The spray unit 212 is coupled to the cylinder portion 133 of the cover 13 with a hose 22. The gas mixture generated in the reagent supply unit 20 is thereby supplied to the inside of the cover 13.

The measuring unit 30 has a configuration in which a display unit 311 and an operation input unit 312 are provided on the upper surface of a box-shaped main body 31. The measuring unit 30 is coupled to the terminals 154 (see FIG. 2(b)) of the detector 15 via a cable 32. The cable 32 is connected to the terminals 154 while passing through the inside of the grip 155. The measuring unit 30 includes a signal processing circuit (not illustrated) such as a central processing unit (CPU) therein, measures strength of a cough induced on the subject based on a detection signal of the sensor 153 (see FIG. 2(b)), and causes the display unit 311 to display a measurement result. The strength of the cough is measured using what is called a peak cough flow (PCF).

For example, an existing spirometer can be used as the filter member 14, the detector 15, and the measuring unit 30. The existing spirometer measures various measurement items other than the strength of a cough (PCF) as a measurement target in the first embodiment and therefore has excessive specification in the first embodiment. It is sufficient that the measuring unit 30 has a configuration and function capable of measuring at least the strength of a cough based on output from the sensor 153.

As illustrated in FIG. 1, when the subject inhales the air by holding the inhalation tool 11 with his (her) mouth, the gas mixture filling the closed space S passes through the holes 121 and is introduced into the pipe 12 as indicated by arrows with dashed-dotted lines in FIG. 2(b). Furthermore, the gas mixture is guided to the inlet port 10a while passing through the inside of the pipe 12, and is inhaled by the subject through the inhalation tool 11. Thus, the inhalation of the reagent induces the subject to cough. When the subject coughs, airflow of the cough travels from the inlet port 10a toward an outlet port 10b while passing through the inside of the pipe 12. In this case, the filter 142 removes foreign bodies such as saliva that are contained in the cough. The sensor 153 outputs a detection signal in accordance with the strength of the cough to the measuring unit 30. The measuring unit 30 measures the strength of the cough (PCF) based on the detection signal, and a measurement result is displayed on the display unit 311. The airflow of the cough that has passed through the sensor 153 is discharged through the outlet port 10b.

In the first embodiment, a physician or the examiner manually measures elapsed time until the subject coughs after the reagent supply unit 20 supplies the gas mixture to the cover 13. The physician or examiner determines an airway protection function of the subject based on the measured elapsed time and the strength of the cough (PCF) displayed on the display unit 311.

Test

The inventors of the present application performed a test of the airway protection function on a plurality of subjects using the airway protection testing apparatus 1 having the above-mentioned configuration. In the test, an existing nebulizer was used as the reagent supply unit 20 and an existing spirometer was used as the filter member 14, the detector 15, and the measuring unit 30. The test was performed on each subject with the following procedures.

(1) A nose clip is mounted on each subject so as to prevent a cough from leaking from his (her) nose.

(2) The reagent supply unit 20 (nebulizers) is filled with a tartaric acid solution at a concentration of 20%, and the gas mixture starts to be sprayed.

(3) Measurement with the spirometer is started.

(4) The inhalation tool 11 of the testing instrument 10 is fit into the mouth of the subject, and inhalation is started.

(5) Time until the subject is induced to cough from the start of the inhalation is measured manually.

(6) Strength of the induced cough (PCF) and a forced vital capacity (FVC) are obtained as measurement results.

FIGS. 4(a) and 4(b) indicate test results of the test. FIG. 4(a) indicates the test results when the subjects were healthy individuals and FIG. 4(b) indicates the test results when the subjects had past histories of aspiration pneumonia.

As illustrated in FIG. 4(a), when the subjects were healthy individuals, the elapsed time until induction of a cough was 1 second for all of the subjects. As a result, it can be evaluated that all of these subjects had sharp sensitivity of the pharynx. When the subjects were healthy individuals, the minimum of the PCFs, each of which indicates the strength of the cough, was 2.5 liters/sec among all of the subjects. As a result, it can be evaluated that all of these subjects had high abilities to expel foreign bodies. Accordingly, this test provided the test results indicating that when the subjects were healthy individuals, all of the subjects had preferable airway protection functions.

Alternatively, as illustrated in FIG. 4(b), when the subjects had the past histories of pneumonia, the elapsed time until induction of the cough was over 20 seconds for each of the subjects. As a result, it can be evaluated that all of these subjects were in states in which their sensitivities of the pharynx were lowered. When the subjects had the past histories of aspiration pneumonia, the PCF indicating the strength of the cough was lower than 0.5 liter/sec for each of the subjects. As a result, it can be evaluated that all of these subjects had low abilities to expel foreign bodies. Accordingly, this test provided the test results indicating that when the subjects had the past histories of aspiration pneumonia, the airway protection functions of all of the subjects were significantly lowered.

Usage of the airway protection testing apparatus 1 having the above-mentioned configuration enables parameter values (induction time of a cough and strength of the cough) in accordance with medical conditions to be obtained. The airway protection function can be properly diagnosed by using the airway protection testing apparatus 1 having the above-mentioned configuration.

In the above-described test, the PCF and the FVC were used as the evaluation parameters. Alternatively, evaluation parameters other than them can be appropriately used.

Effects of First Embodiment

The configuration of the first embodiment can provide the following effects.

Usage of the testing instrument 10 can simultaneously measure elapsed time until induction of a cough and strength of the cough. The cough caused by using the testing instrument 10 is not a voluntary cough intended by the subject but an involuntary cough reflexively caused by a reagent. The involuntary cough can be measured by using the testing instrument 10, thereby grasping the sensitivity of the pharynx and the ability to expel foreign bodies as an original airway protection function of the subject. Accordingly, the airway protection function of the subject can be properly diagnosed by using the testing instrument 10.

As illustrated in FIG. 2(b), the inhalation tool 11 to be held in the mouth of the subject is installed on the inlet port 10a in a detachable manner. With this configuration, the inhalation tool 11 can be appropriately replaced, thereby testing the airway protection function hygienically.

As illustrated in FIGS. 2(a) and 2(b), the cover 13 is detachable from the pipe 12. The cover 13 can therefore be detached from the pipe 12 appropriately, and then the cover 13 and the pipe 12 can be cleaned by washing or the like. Accordingly, the testing instrument 10 can be kept hygienic, and clogging of the holes 121 can be prevented by cleaning.

As illustrated in FIG. 2(a), the holes 121 are formed in the pipe 12. The proper amount of reagent can therefore be smoothly introduced into the pipe 12 when the reagent is inhaled while reducing the size of the individual holes 121. Furthermore, the reduction in size of the individual holes 121 can prevent airflow generated by the subject's cough from leaking into the cover 13 through the holes 121. The airflow of the cough can therefore be smoothly guided to the outlet port 10b, thereby measuring the strength of the cough with high accuracy.

As illustrated in FIGS. 2(a) and 2(b), the holes 121 are formed so as to gradually become closer to the inlet port 10a as the holes 121 approach the inner surface of the pipe 12 from the outer surface thereof. Thus, the reagent gas mixture can be made to smoothly travel toward the inlet port 10a when the reagent is inhaled.

The PCF indicating the strength of the cough is displayed on the display unit 311 of the measuring unit 30. This display enables a physician, an examiner, or the like to determine whether the subject has a disorder in the airway protection function by checking the display.

Second Embodiment

In the first embodiment, the reagent supply unit 20 and the measuring unit 30 are configured as the separate bodies. In a second embodiment, they are integrated with each other as one unit.

Figure 5:
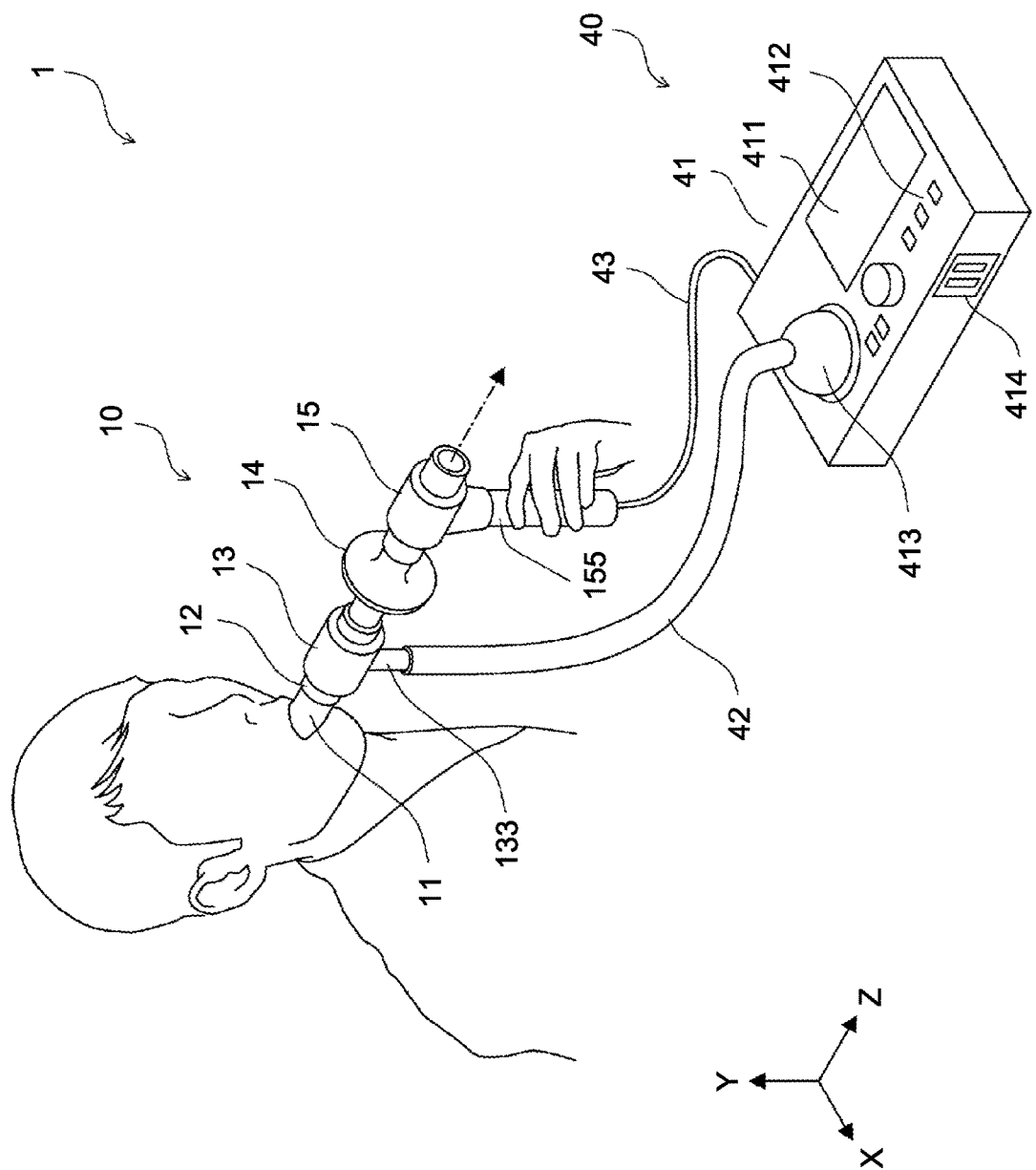
FIG. 5 is a view illustrating the configuration of an airway protection testing apparatus according to a second embodiment.

FIG. 5 is a perspective view illustrating the configuration of the airway protection testing apparatus 1 according to the second embodiment.

As illustrated in FIG. 5, the testing instrument 10 has the same configuration as that in the above-described first embodiment. A testing unit 40 has a configuration in which a display unit 411, an operation input unit 412, and a spray unit 413 are provided on the upper surface of a box-shaped main body 41. A speaker 414 is provided on the side surface of the main body 41. The testing unit 40 is coupled to the terminals 154 (see FIG. 2B) of the detector 15 via a cable 43. The cable 43 is connected to the terminals 154 while passing through the inside of the grip 155. The spray unit 413 discharges a reagent gas mixture that is generated in the main body 41. The spray unit 413 is coupled to the cylinder portion 133 of the cover 13 with a hose 42. The gas mixture generated in the testing unit 40 is thereby supplied into the cover 13.

FIG. 6 is a diagram illustrating the block configuration of the airway protection testing apparatus 1 according to the second embodiment.

As illustrated in FIG. 6, the testing unit 40 includes a controller 401, a reagent supply unit 402, and a measuring unit 403 in addition to the display unit 411, the operation input unit 412, and the speaker 414. The reagent supply unit 402 includes the spray unit 413.

The controller 401 includes a processing unit such as a CPU and a storage 401a. The storage 401a includes a storage device such as a read only memory (ROM) and a random access memory (RAM). The controller 401 controls each unit in accordance with a control program stored in the storage 401a. The storage 401a stores therein the above-mentioned control program and is used as a work area when the control program is executed.

The reagent supply unit 402 nebulizes the reagent (tartaric acid solution) contained in a reagent container 402a to generate the gas mixture obtained by mixing droplets of the reagent with the air. The reagent supply unit 402, for example, generates fine droplets based on the principle of spray using high-speed airflow, or makes the reagent into droplets by an ultrasonic oscillator to generate the gas mixture by causing the droplets to flow on the air from a fan.

The measuring unit 403 starts a time counting operation in accordance with an instruction from the controller 401 and measures elapsed time until the subject is induced to cough after the reagent starts to be supplied. In this case, the measuring unit 403 detects the induction of the cough based on a detection signal from the detector 15 (sensor 153). The measuring unit 403 measures strength of the induced cough (PCF) with the detection signal from the detector 15 (sensor 153) in accordance with an instruction from the controller 401. When detecting the induction of the cough based on the detection signal from the detector 15 (sensor 153), the measuring unit 403 outputs information indicating the measured elapsed time and the strength of the cough (PCF) to the controller 401.

In the cough measuring operation, the measuring unit 403 calculates a flow rate (liters/sec) of the cough flowing toward the outlet port 10b in the detector 15, for example, based on the detection signal from the sensor 153. The measuring unit 403 determines that the cough has been induced when the flow rate is higher than a predetermined threshold, and a period of time until the flow rate is lower than the threshold again is set to a coughing period. The measuring unit 403 detects a maximum value (peak value) of the flow rate during the coughing period set in this manner as the strength of the cough (PCF). A change speed of the detection signal from the sensor 153 may be obtained as the flow rate of the cough.

FIG. 7 is a flowchart illustrating control of the airway protection testing apparatus according to the second embodiment. The measurement processing is performed after the nose clip is mounted on the subject and the subject holds the inhalation tool 11 of the testing instrument 10 with his (her) mouth as measurement preparation operations.

When a measurement start instruction is input through the operation input unit 412 (YES at S11), the controller 401 causes the measuring unit 403 to start measurement of elapsed time and measurement of a cough (S12). Simultaneously with this, the controller 401 causes the reagent supply unit 402 to start to spray the reagent (S13). The controller 401 continues these operations until the measuring unit 403 detects the cough (S14).

Thereafter, when the subject is induced to cough and the controller 401 receives the information indicating the elapsed time and the strength of the cough from the measuring unit 403, the controller 401 determines that the cough has been detected (YES at S14) and causes the reagent supply unit 402 to finish to spray the reagent (S15). The controller 401 controls to store the received the information indicating the elapsed time and the strength of the cough in the storage 401a and causes the display unit 411 to display the information (S16). Furthermore, the controller 401 refers to the received elapsed time and strength of the cough and determines whether the elapsed time is equal to or longer than a predetermined threshold Ts and the strength of the cough is equal to or weaker than a predetermined threshold Ps (S17). When the condition is satisfied (YES at S17), the controller 401 adds information indicating that the subject has a risk of an airway protection disorder onto a screen on the display unit 411 (S18). Alternatively, when the above-mentioned condition is not satisfied (NO at S17), the controller 401 adds information indicating that the subject has no risk of the airway protection disorder onto the screen on the display unit 411 (S19).

Figure 8A:
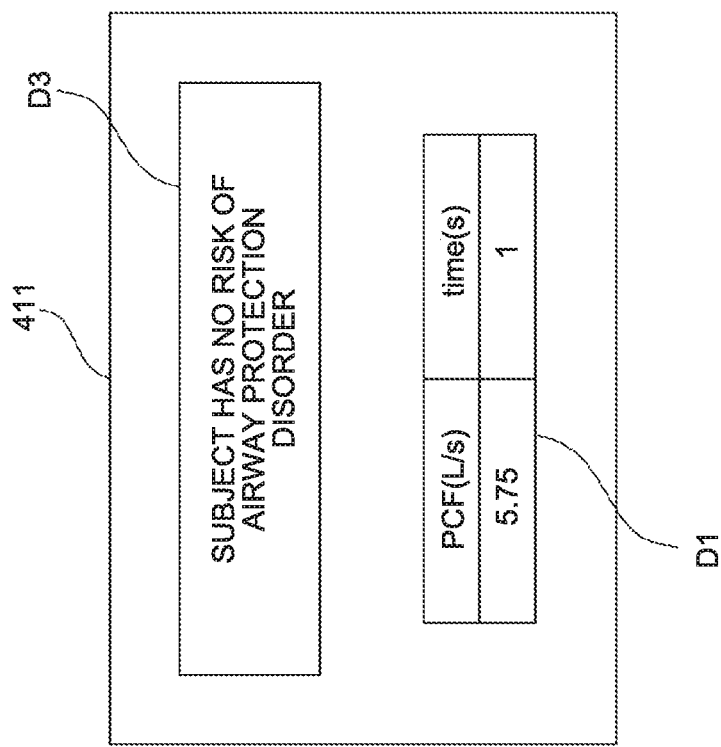
FIG. 8A and FIG. 8B include views each illustrating an example of a display screen according to the second embodiment.
Figure 8B:
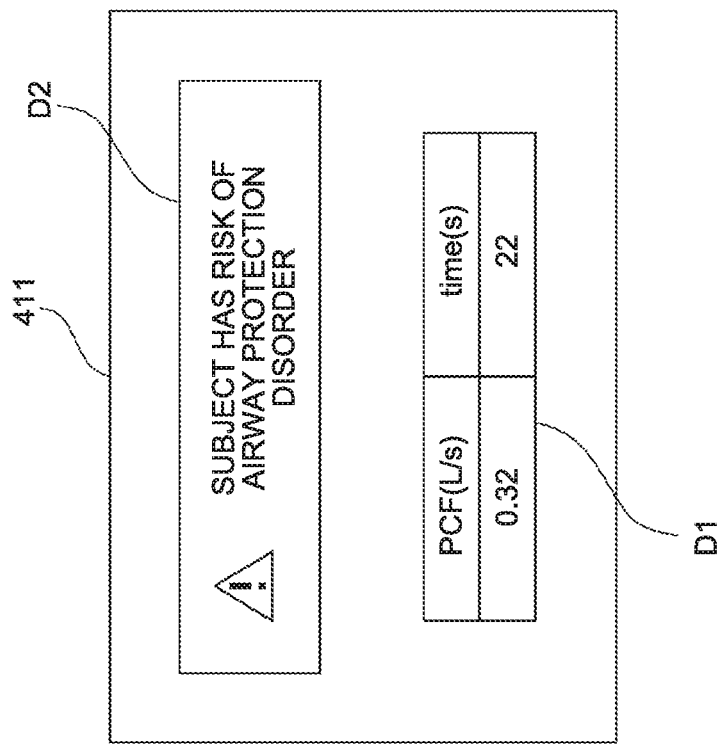

FIGS. 8(a) and 8(b) are views indicating the screens on the display unit 411 when the respective pieces of processing at S18 and S19 are performed.

As illustrated in FIG. 8(a), when the condition that the elapsed time measured by the measuring unit 403 is equal to or longer than the predetermined threshold Ts and the strength of the cough is equal to or weaker than the predetermined threshold Ps is satisfied, display D1 indicating the elapsed time (time) and the strength of the cough (PCF) and display D2 indicating that the subject has the risk of the airway protection disorder are displayed on the display unit 411. By contrast, when the condition that the elapsed time measured by the measuring unit 403 is equal to or longer than the predetermined threshold Ts and the strength of the cough is equal to or weaker than the predetermined threshold Ps is not satisfied, the display D1 and display D3 indicating that the subject has no risk of the airway protection disorder are displayed on the display unit 411. These displays enable a physician, an examiner, or the like to easily determine whether the subject has the risk of the airway protection disorder.

Effects of Second Embodiment

The second embodiment also provides the same effects as those provided in the first embodiment. In addition, the second embodiment can provide the following effects.

The measuring unit 403 measures elapsed time until induction of a cough after a reagent starts to be sprayed. Time and effort for measuring the elapsed time manually can therefore be saved. Furthermore, the elapsed time (time) and the strength of the cough (PCF) are displayed on the display unit 411. This display enables a physician, an examiner, or the like to simultaneously grasp the strength of the cough and the elapsed time until the induction of the cough and to smoothly and easily determine whether the subject has the disorder in the airway protection function by checking the display on the display unit 411.

In addition, in the second embodiment, as illustrated in FIGS. 8A and 8B, the screen contains the displays D2 and D3 regarding the risk of the airway protection disorder. With this display, the risk of the airway protection disorder can be easily grasped also in nursing and caring facility and the like in which there is no person who has expert knowledge, such as a physician and an examiner. Persons in charge in the nursing and caring facility and the like can therefore take measures of causing the subject having the risk of the airway protection disorder to undergo medical examination by a specialist and so on appropriately, thereby reducing the possibility that the subject suffers from aspiration pneumonia.

Furthermore, as illustrated in FIG. 5, the constituent units other than the testing instrument 10 are intensively installed in one testing unit 40. With this configuration, the airway protection testing apparatus 1 can be easily carried and a test operation can also be easily performed.

In the flowchart illustrated in FIG. 7, the pieces of processing at S17 to S19 may be omitted. In this case, the displays D2 and D3 are omitted from FIGS. 8(a) and 8(b). Also in this case, persons who have the expert knowledge, such as a physician and an examiner, can determine whether the subject has the risk of the airway protection disorder based on the display D1. In this case, persons who do not have the expert knowledge, such as persons in charge in the nursing and caring facility, cannot determine whether the subject has the risk of the airway protection disorder based on the display D1. This mode is therefore considered to be useful when the airway protection testing apparatus 1 is used in medical institution.

Alternatively, in the flowchart illustrated in FIG. 7, the display processing at S16 may be omitted. In this case, the display D1 is omitted from FIGS. 8(a) and 8(b). Not only persons who have the expert knowledge, such as a physician and an examiner, but also persons in charge in the nursing and caring facility can determine whether the subject has the risk of the airway protection disorder based on the displays D2 and D3. In this case, a physician, an examiner, or the like cannot determine the level of the airway protection disorder of the subject because there is no display D1. This mode is therefore considered to be useful when the airway protection testing apparatus 1 is used in non-medical institution.

Although the test results are displayed on the display unit 411 in the flowchart in FIG. 7, sound indicating a display result may be output from the speaker 414 in addition to the display or instead of the display. For example, predetermined warning sound may be output from the speaker 414 only in the processing at S18 or different types of sound may be output from the speaker 414 in the processing at S18 and the processing at S19. Alternatively, announcement reading notifications corresponding to displays in the pieces of processing at S18 and S19 may be output from the speaker 414.

The condition for determining whether the subject has the risk of the airway protection disorder is set to the condition indicated by the processing at S17 in the flowchart in FIG. 7. However, conditions other than that may be used. For example, a method in which it is determined that the subject has the risk of the airway protection disorder when the elapsed time is significantly long or a method in which it is determined that the subject has the risk of the airway protection disorder when the strength of the cough is significantly weak may be used together with the determination condition indicated by the processing at S17 or instead of the determination condition indicated by the processing at S17. Alternatively, whether the subject has the risk of the airway protection disorder may be determined by comparing a value, which is obtained by substituting the elapsed time and the strength of the cough into a predetermined expression, with a threshold.

Third Embodiment

In the second embodiment, the testing instrument 10 and the testing unit 40 are configured as the separate bodies. In a third embodiment, they are integrated with each other as one unit.

Figure 9:
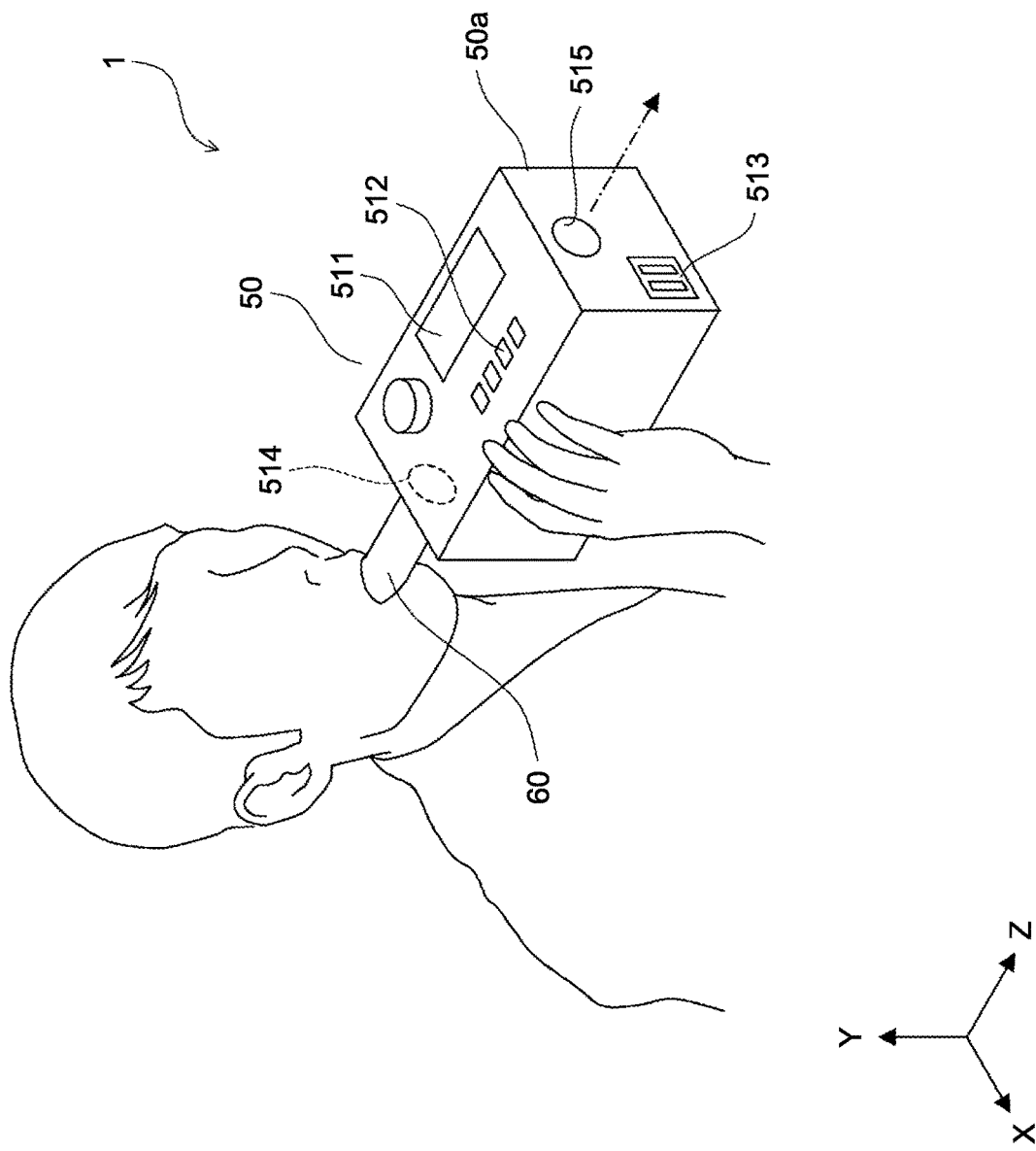
FIG. 9 is a view illustrating the configuration of an airway protection testing apparatus according to a third embodiment.

FIG. 9 is a perspective view illustrating the configuration of the airway protection testing apparatus 1 according to the third embodiment.

As illustrated in FIG. 9, a main body 50 of the airway protection testing apparatus 1 is constructed from a box-shaped housing 50a. A display unit 511 and an operation input unit 512 are provided on the upper surface of the main body 50, and a speaker 513 is provided on the side surface of the main body 50. Furthermore, circular holes 514 and 515 are provided in the side surfaces of the main body 50, the side surfaces facing in the positive and negative directions of the Z-axis, respectively.

The testing instrument 10 is accommodated in the housing 50a. The testing instrument 10 has, for example, a configuration in which the grip 155 is omitted from the configuration illustrated in FIG. 1. The inlet port 10a of the testing instrument 10 is exposed to the outside through the hole 514, and the outlet port 10b of the testing instrument 10 is exposed to the outside through the hole 515. An inhalation tool 60 is fit into the inlet port 10a in a detachable manner. The testing instrument 10 is desirably detachable from the housing 50a by, for example, opening the upper surface of the housing 50a.

Constituent blocks corresponding to the controller 401, the storage 401a, the reagent supply unit 402, the reagent container 402a, and the measuring unit 403 illustrated in FIG. 6 are accommodated in the housing 50a. These components are appropriately connected to each other with pipes or wirings in the housing 50a. Also in the third embodiment, the same control as that illustrated in FIG. 7 and the same display as that illustrated in FIG. 8 are performed. A test start instruction is input by, for example, pushing, by the subject, a start button on the operation input unit 512 with his (her) finger.

Effects of Third Embodiment

The third embodiment also provides the same effects as those provided in the second embodiment.

In addition, with the third embodiment, the testing instrument 10 and the testing unit 40 are integrated with each other as one unit. The airway protection testing apparatus 1 can therefore be carried more easily and a test operation can be performed more easily than in the second embodiment.

In the third embodiment, as illustrated in FIG. 9, the airway protection testing apparatus 1 and a face of the subject are close to each other, thereby arranging a detection unit for detecting that the subject has held the inhalation tool 60 with his (her) mouth on the airway protection testing apparatus 1. An optical sensor, a miniature camera, or the like can be used as the detection unit. When such a detection unit is arranged, spray of a reagent, measurement of elapsed time, and detection of a cough may be started in response to the detection that the subject has held the inhalation tool 60 with his (her) mouth. The airway protection function of the subject can thereby be diagnosed more easily with high accuracy.

Modifications

Although the embodiments of the present invention have been described hereinbefore, the above-mentioned embodiments do not limit the present invention and the embodiments of the present invention can also be variously changed.

For example, although the holes 121 are formed so as to gradually become closer to the inlet port 10a as the holes approach the inner surface of the pipe 12 from the outer surface thereof as illustrated in FIG. 2(b) in the first embodiment, a method of forming the holes 121 is not limited thereto. As illustrated in FIG. 10(a), the holes 121 may be formed such that the positions of the holes 121 do not vary between the outer surface and the inner surface, for example. Alternatively, as illustrated in FIG. 10(b), the holes 121 may be formed so as to gradually become farther from the inlet port 10a as the holes 121 approach the inner surface of the pipe 12 from the outer surface thereof. The hole formation mode illustrated in FIG. 2(b) and the hole formation mode illustrated in FIG. 10(a) or 10(b) may be mixed. The sizes of the holes 121 may not be necessarily constant.

When the holes 121 are formed as illustrated in FIG. 10(b), airflow generated by a cough of the subject is difficult to leak into the cover 13 (closed space S) through the holes 121. The airflow of the cough can therefore be smoothly introduced to the outlet port 10b, thereby detecting strength of the cough with high accuracy.

As illustrated in FIG. 11(a), a disc-like stopper 134 blocking a flow path of the cylinder portion 133 and a knob 135 for opening and closing the stopper 134 may be provided. In the configuration in FIG. 11(a), the stopper 134 is coupled to the knob 135 and is supported on the cylinder portion 133 in a rotatable manner about the Z axis. When the knob 135 is turned, the stopper 134 rotates to open the flow path of the cylinder portion 133.

With this configuration, even when the reagent supply unit 20 starts a reagent spray operation, the stopper 134 blocks travelling of the reagent gas mixture. When the subject holds the inhalation tool 11 with his (her) mouth, and then, the knob 135 is turned, the reagent gas mixture enters the closed space S and is inhaled by the subject. Accordingly, in this configuration example, turning the knob 135 triggers the start of inhalation of the gas mixture. The elapsed time until the cough is induced after the gas mixture starts to be inhaled can therefore be measured smoothly and accurately.

Although in the configuration example illustrated in FIG. 11(a), turning the knob 135 causes the stopper 134 to be opened, the stopper 134 may be opened by a push-type switch. The employment of the switch can control opening and closing of the stopper 134 more easily. Furthermore, the stopper 134 may be controlled to be opened and closed electrically by an operation with buttons. In this case, opening and closing buttons may be provided on the testing instrument 10 or may be provided on the measuring unit 30 illustrated in FIG. 1 or the testing unit 40 illustrated in FIG. 5.

Although the pipe 12 and the cover 13 are configured as the separate bodies and can be detachable from each other as illustrated in FIGS. 2(a) and 2(b) in the first embodiment, a cylinder portion 122 may be integrally formed on the lower surface of the pipe 12 and the holes 121 may be positioned in the cylinder portion 122 as illustrated in FIG. 11(b). In this case, the hose 22 illustrated in FIG. 1 is coupled to the cylinder portion 122.

With this configuration, the cover 13 is omitted, thereby reducing the number of components and simplifying the configuration. However, clogging of the holes 121 is more difficult to be prevented than in the first embodiment because it is difficult to clean the holes 121. Furthermore, the number of holes 121 is smaller than that in the above-mentioned first embodiment. This makes the reagent gas mixture difficult to be introduced to the inlet port 10a. For this reason, the holes 121 are required to be increased in size in comparison with the above-mentioned first embodiment. The increase in size of the holes 121 causes the airflow of the cough to be easy to leak from the holes 121, and the cough detection accuracy may be lowered. In consideration of these circumstances in a comprehensive manner, it is considered that the configuration using the cover 13 as in the above-mentioned first embodiment is desirable.

Although the cover 13 and the pipe 12 are integrated with each other by fitting the pipe 12 into the openings 132 of the cover 13 in the above-mentioned first embodiment, a method for integrating the cover 13 and the pipe 12 is not limited thereto. For example, a cover 16 illustrated in FIGS. 12(a) and 12(b) may be used instead of the cover 13. FIG. 12(b) is a cross-sectional view of a constitution body obtained by integrating the cover 16 and the pipe 12 and corresponds to the cross-sectional view in FIG. 3. FIG. 12(a) is a cross-sectional view of the cover 16 alone when the pipe 12 is removed from FIG. 12(b).

The cover 16 illustrated in FIG. 12(a) has a configuration in which wall portions 163 extending in the vertical direction are superimposed on the upper surfaces of a constituent body obtained by cutting the cover 13 illustrated in FIG. 2(a) along a plane that is parallel to the X-Z plane and contains the center axis L and then removing the upper portion of the cover 13. A flange portion 161 corresponds to the flange portion 131 of the cover 13 illustrated in FIG. 2, and a cylinder portion 162 corresponds to the cylinder portion 133 of the cover 13 illustrated in FIG. 2. The flange portion 161 has only a lower semicircle portion, and the wall portions 163 are continuously provided above the flange portion 161. In the same manner as FIG. 2(a), the flange portion 161 is also provided at the side facing in the negative direction of the Z-axis.

A pressing plate 164 is supported on the upper surfaces of the wall portions 163 in a rotatable manner by a support axis 165. That is to say, the pressing plate 164 is rotatable about 165. A U-shaped cut 164a having a depth in the positive direction of the Z-axis is provided at an end portion of the pressing plate 164. When the pressing plate 164 rotates forward (in the negative direction of the Z-axis), the cut 164a is engaged with a shaft portion of a fastening tool 166. A head portion is provided on the shaft portion of the fastening tool 166. Upward movement of the pressing plate 164 is therefore restricted.

When the pipe 12 and the cover 16 are integrated with each other, the upper surface of the cover 16 is opened by rotationally moving the pressing plate 164 backward (in the positive direction of the Z-axis). In this state, the pipe 12 is placed on the cover 16. The holes 121 are formed over the semi-circumference of the pipe 12. The pipe 12 is placed on the cover 16 such that a region with the holes 121 is located at the lower side. Thereafter, the pressing plate 164 is rotated forward (in the negative direction of the Z-axis) to cause the cut 164a to be engaged with the shaft portion of the fastening tool 166. With this engagement, the pipe 12 and the cover 16 are integrated with each other as illustrated in FIG. 12(b).

As illustrated in FIG. 12B, in this configuration example, a flat surface 123 is formed on the upper surface of the pipe 12. The flat surface 123 is pressed by the pressing plate 164 such that the pipe 12 is positioned at a predetermined rotational position. In this case, the flat surface 123 is slightly higher than the lower surface of the pressing plate 164. The pipe 12 therefore receives downward force by the pressing plate 164 to be pressed against the cover 16. When the pipe 12 and the cover 16 are integrated with each other in this manner, the closed space S is formed so as to cover the holes 121. When the reagent gas mixture flows into the closed space S from the cylinder portion 162, the closed space S is filled with the gas mixture, and the gas mixture is guided into the pipe 12 through the holes 121. The subject then inhales the reagent gas mixture.

Although the sizes of the holes 121 are constant in the above-mentioned embodiments, the sizes of the holes 121 may be changeable, and the mixed amount of the reagent may be controllable by changing the sizes of the holes 121.

FIG. 13(a) illustrates a configuration example in which the sizes of the holes 121 are changeable. FIG. 13(a) illustrates, as a sectional view, only the configuration in the vicinity of the cover 13 in the testing instrument 10. FIG. 13(a) is a sectional view when the testing instrument 10 is evenly cut by a plane that is parallel to the Y-Z plane in the same manner as FIG. 2(b).

As illustrated in FIG. 13(a), in this configuration example, the pipe 12 in the first embodiment is changed to two cylindrical pipes 12a and 12b. In the configuration example, the outer diameter of an end portion of the pipe 12b at the side facing in the negative direction of the Z-axis is substantially identical to the inner diameter of an end portion of the pipe 12a at the side facing in the positive direction of the Z-axis. The two pipes 12a and 12b are integrated with each other by fitting these two end portions with each other. In the thus combined state, the pipe 12a is rotatable about an axis parallel to the Z axis with respect to the pipe 12b. Furthermore, holes 121a and 121b that oppose each other in the combined state are formed in the pipes 12a and 12b, respectively.

FIGS. 13B and 13C are cross-sectional views obtained by cutting the pipes 12a and 12b, which are combined as illustrated in FIG. 13A, along a plane parallel to the X-Y plane at a position of the holes 121a and 121b.

As illustrated in FIG. 13(b), the eight long holes 121a are formed evenly in the circumferential direction on the end portion of the pipe 12a that is fit with the end portion of the pipe 12b. The long holes 121a have contours elongated in the circumferential direction of the pipe 12a. In the same manner, eight long holes 121b are also formed evenly in the circumferential direction on the end portion of the pipe 12b that is fit with the end portion of the pipe 12a. The long holes 121b have contours elongated in the circumferential direction of the pipe 12b. In this configuration example, the dimensions of the long holes 121a in the circumferential direction and the dimensions of the long holes 121b in the circumferential direction are the same.

In the state illustrated in FIG. 13(a), the long holes 121a completely match with the long holes 121b, and the sizes of the holes communicating between the closed space S and the inside of the pipes 12a and 12b illustrated in FIG. 13(a) are therefore maximum. When the pipe 12a is rotated in the circumferential direction from this state as illustrated in FIG. 13(c), overlapped portions of the long holes 121a and the long holes 121b are decreased. The sizes of the holes communicating between the closed space S and the inside of the pipes 12a and 12b illustrated in FIG. 13(a) are therefore made smaller than those in the case of FIG. 13(b).

In this configuration example, the sizes of the holes communicating between the closed space S and the inside of the pipes 12a and 12b can be changed by rotating the pipe 12a in this manner. The mixed amount of the reagent can be desirably controlled by providing a changing mechanism for changing the sizes of the holes.

Although the dimensions of the long holes 121a in the circumferential direction and the dimensions of the long holes 121b in the circumferential direction are the same in the configuration example of FIGS. 13A to 13C, the dimensions of the long holes 121a in the circumferential direction may be different from the dimensions of the long holes 121b in the circumferential direction. Furthermore, the eight long holes 121a formed in the pipe 12a may not have the same dimension in the circumferential direction. Similarly, the eight long holes 121b formed in the pipe 12b may not have the same dimension in the circumferential direction. Moreover, the number of the long holes 121a and 121b formed in the pipes 12a and 12b is not limited to eight and may be another number. Circular holes may be formed instead of the long holes 121a and 121b. Other desirable shapes, sizes, and arrangement positions of the holes may be employed as long as the overlap amount of the two holes can be changed by relatively rotating the pipes 12a and 12b in the circumferential direction.

Although the overlap amount of the two long holes 121a and 121b is changed by relatively rotating the pipes 12a and 12b in the circumferential direction in the configuration example of FIGS. 13(a) to 13(c), the overlap amount of the two long holes 121a and 121b may be changed by relatively moving the pipes 12a and 12b in the lengthwise direction as illustrated in FIGS. 14(a) and 14(b).

In the configuration example of FIGS. 14(a) and 14(b), in a state in which the end portion of the pipe 12a at the side facing in the positive direction of the Z-axis and the end portion of the pipe 12b at the side facing in the negative direction of the Z-axis are completely fit with each other as illustrated in FIG. 14(a), holes 121c in the pipe 12a and holes 121d in the pipe 12b completely match with each other. From this state, when the pipe 12a is moved in the negative direction of the Z-axis as illustrated in FIG. 14(b), the overlap amount of the two long holes 121c and 121d is decreased. The sizes of the holes communicating between the closed space S and the inside of the pipes 12a and 12b are therefore made smaller than those in the case of FIG. 14(a).

In this manner, the configuration example of FIGS. 14(a) and 14(b) can also change the sizes of the holes communicating between the closed space S and the inside of the pipes 12a and 12b in the same manner as the configuration example of FIGS. 13(a) to 13(c). The mixed amount of the reagent can thereby be desirably controlled. The holes 121c and 121d may have contours elongated in the Z-axis direction or may have other shapes. In the same manner as the configuration example of FIGS. 13(a) to 13(c), other desirable shapes, sizes, and arrangement positions of the holes may be employed as long as the overlap amount of the two holes can be changed by relatively moving the pipes 12a and 12b in the lengthwise direction.

In the configuration example of FIGS. 13(a) to 13(c), a member that restricts a rotational movement range of the pipe 12a to a range in which the two long holes 121a and 121b oppose each other completely or at least partially is desirably provided. Furthermore, a guide member for rotating the pipe 12a in a state in which the two pipes 12a and 12b are completely fit with each other is desirably provided.

In the configuration example of FIGS. 14(a) and 14(b), a unit that restricts a movement range of the pipe 12a in the lengthwise direction to a range in which the two long holes 121c and 121d oppose each other completely or at least partially is desirably provided. Furthermore, a guide unit for moving the pipe 12a in the lengthwise direction in a state in which the two pipes 12a and 12b are not deviated from each other in the circumferential direction is desirably provided.

Although the pipe 12, the support portion 141 of the filter member 14, and the cylindrical members 151a and 151b of the detector 15 are coupled to each other to configure the "pipe portion" described in the claims in the above-mentioned first embodiment, a method for configuring the "pipe portion" is not limited thereto. For example, the "pipe portion" is not necessarily required to be configured by coupling other separate members and may be configured with one member. Furthermore, the "pipe portion" may be configured by coupling only the detector 15.

Although the filter member 14 is effective for removing flown foreign bodies contained in the cough, it may be appropriately omitted from the configuration of the testing instrument 10 according to the invention. An arrangement position of the sensor 153 is not limited to the position in the first embodiment and can be appropriately changed to another position as long as the arrangement position is a position at which the strength of the subject's cough can be detected. The arrangement position of the filter member 14 can also be appropriately changed.

For example, the filter member 14 may be arranged between the inlet port 10a and the pipe 12 as illustrated in FIG. 15. This arrangement enables the foreign bodies and the like contained in the cough to be prevented from adhering to the pipe 12 and the cover 13, thereby keeping the inside of the testing instrument 10 more hygienic. In this case, the filter member 14 is preferably arranged such that the filter 142 is close to the rear end of the inhalation tool 11 as much as possible. This arrangement enables the foreign bodies and the like to be prevented from adhering to the inside of the filter member 14. The filter 142 may be integrated with the inhalation tool 11. This causes the filter 142 to be also disposable together with the inhalation tool 11 but the inside of the testing instrument 10 can be hygienically kept more reliably.

In the configuration illustrated in FIG. 15, the sensor 153 may be arranged between the filter 142 and the pipe 12. In the configuration illustrated in FIG. 15, the foreign bodies and the like contained in the cough do not adhere to the sensor 153 even when the sensor 153 is arranged between the filter 142 and the pipe 12 because the filter 142 is positioned at a just rear side of the inhalation tool 11.

Furthermore, a display mode of the test result is not limited to the display modes illustrated in FIGS. 8(a) and 8(b) and can be appropriately modified. A waveform or the like of the cough, another parameter value, or the like may be added as a display target. Moreover, the number, shapes, and sizes of the holes 121 can also be appropriately changed. The material of the testing instrument 10 is not limited to resin, and another material such as metal can also be used.

In addition, embodiments of the present invention can be variously changed appropriately within a range of a technical idea described in the claims.

The invention claimed is:

1. A testing kit that is used for testing an airway protection function, the testing kit comprising:
a testing instrument including:
a pipe portion continuous from an inlet port to an outlet port, the pipe portion having a plurality of holes penetrating the pipe portion from an outer surface of the pipe portion to an inner surface of the pipe portion, the holes being provided for guiding a reagent gas mixture to the inside of the pipe portion, and
a guide portion covering all of the holes to form a closed space and guiding the reagent gas mixture to the closed space from an inflow port;
a reagent supply unit including a sprayer coupled to the inflow port and supplying the reagent gas mixture to the inflow port; and
a sensor for detecting a strength of airflow that is discharged from the outlet port,
wherein the holes are provided closer to the inlet port than the outlet port, and
wherein the sensor is provided closer to the outlet port than the inlet port.

2. The testing kit according to claim 1,
wherein an inhalation tool to be held in the mouth of a subject is installed on the inlet port in a detachable manner.

3. The testing kit according to claim 1,
wherein the guide portion is configured to be detachable from the pipe portion, and
wherein, when the guide portion is mounted on the pipe portion, the closed space is formed around the holes, and the closed space and the inflow port communicate with each other.

4. The testing kit according to claim 3,
wherein the guide portion has an opening into which the pipe portion is fit in a detachable manner, and has such a shape that, when the pipe portion is fit into the opening, the closed space is formed around the holes, and the closed space and the inflow port communicate with each other.

5. The testing kit according to claim 1,
wherein the holes are formed so as to gradually become closer to the inlet port as the holes approach the inner surface of the pipe portion from the outer surface of the pipe portion.

6. The testing kit according to claim 1,
wherein the holes are formed so as to gradually become farther from the inlet port as the holes approach the inner surface of the pipe portion from the outer surface of the pipe portion.

7. The testing kit according to claim 1, further comprising:
a stopper provided between the closed space and the inflow port and blocking a flow path continuous from the inflow port to the holes; and
an opening and closing member opening and closing coupled to the stopper and configured to rotate the stopper to open and close the stopper.

8. The testing kit according to claim 1,
wherein the pipe portion includes a first pipe having a plurality of first holes and a second pipe having a plurality of second holes, and the first pipe is fit into the second pipe such that the first and second pipes are rotatable or movable relative to each other, and
wherein the holes of the pipe portion are formed by positioning the first and second pipes such that the first holes of the first pipe overlap the second holes of the second pipe, and a size of each hole of the pipe portion is changeable by moving or rotating the first and second pipes relative to each other.

9. An airway protection testing apparatus comprising:
the testing kit according to claim 1;
a processor measuring the strength of airflow that is discharged from the outlet port based on a detection signal from the sensor; and
a screen displaying information based on a measurement result obtained by the processor.

10. The airway protection testing apparatus according to claim 9,
wherein the processor further measures, based on the detection signal from the sensor, an elapsed time until the airflow is generated in the outlet port after the gas mixture starts to be supplied to the inflow port, and
wherein the screen further displays information based on the elapsed time.

11. The airway protection testing apparatus according to claim 9,
wherein the processor further measures, based on the detection signal from the sensor, an elapsed time until the airflow is generated in the outlet port after the gas mixture starts to be supplied to the inflow port, and determines a risk of an airway protection disorder based on the strength of the airflow and the elapsed time, and
wherein the screen displays information based on a determination result of the risk.

12. The airway protection testing apparatus according to claim 9,
wherein the testing kit the sensor, the processor, and the screen are accommodated in one housing.

13. The testing kit according to claim 1,
wherein the guide portion is provided so as to cover an entire circumference of a part of the pipe portion, and
wherein the holes are provided at different locations across an area that is covered by the guide portion.

14. An airway protection testing apparatus for testing an airway protection function, the airway protection testing apparatus comprising:
a testing instrument including:
a pipe portion continuous from an inlet port to an outlet port, the pipe portion having at least one hole penetrating the pipe portion from an outer surface of the pipe portion to an inner surface of the pipe portion, and a guide portion covering the hole and guiding a reagent gas mixture to the hole from an inflow port;

a reagent supply unit that includes a sprayer coupled to the inflow port and supplying the reagent gas mixture to the inflow port;

a sensor for detecting a strength of airflow that is discharged from the outlet port;

a processor measuring the strength of the airflow that is discharged from the outlet port based on a detection signal from the sensor; and a screen displaying information based on a measurement result obtained by the processor, wherein the processor further measures, based on the detection signal from the sensor, elapsed time until the airflow is generated in the outlet port after the gas mixture is started to be supplied to the inflow port, and wherein the screen further displays information based on the elapsed time, wherein the holes are provided closer to the inlet port than the outlet port, and wherein the sensor is provided closer to the outlet port than the inlet port.

15. The airway protection testing apparatus according to claim 14, wherein the processor further determines a risk of an airway protection disorder based on the strength of the airflow and the elapsed time, and wherein the screen displays information based on a determination result of the risk.

16. The airway protection testing apparatus according to claim 14, wherein the testing instrument, the reagent supply unit, the sensor, the processor, and the screen are accommodated in one housing.

* * * * *